(12) United States Patent
Alderfer et al.

(10) Patent No.: US 10,000,559 B2
(45) Date of Patent: *Jun. 19, 2018

(54) ANTI-PHF-TAU ANTIBODIES AND THEIR USES

(71) Applicant: Janssen Biotech, Inc., Horsham, PA (US)

(72) Inventors: Christopher Alderfer, Spring House, PA (US); Dariusz Janecki, Kobenhavn O (DK); Xuesong Liu, Spring House, PA (US); Melissa Murdock, Spring House, PA (US); Sheng-Jiun Wu, Spring House, PA (US); Marc Mercken, Beerse (BE); Marc Vandermeeren, Beerse (BE); Thomas Malia, Spring House, PA (US)

(73) Assignee: Janssen Biotech, Inc., Horsham, PA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/646,865

(22) Filed: Jul. 11, 2017

(65) Prior Publication Data

US 2017/0355758 A1 Dec. 14, 2017

Related U.S. Application Data

(63) Continuation of application No. 15/138,635, filed on Apr. 26, 2016, now Pat. No. 9,745,371, which is a continuation of application No. 14/363,888, filed as application No. PCT/US2012/070486 on Dec. 19, 2012, now Pat. No. 9,371,376.

(60) Provisional application No. 61/577,817, filed on Dec. 20, 2011.

(51) Int. Cl.
    *C07K 16/18* (2006.01)
    *A61K 39/00* (2006.01)

(52) U.S. Cl.
    CPC ........ *C07K 16/18* (2013.01); *A61K 2039/505* (2013.01); *C07K 2317/24* (2013.01); *C07K 2317/34* (2013.01); *C07K 2317/56* (2013.01); *C07K 2317/565* (2013.01); *C07K 2317/76* (2013.01); *C07K 2317/92* (2013.01)

(58) Field of Classification Search
    None
    See application file for complete search history.

(56) References Cited

U.S. PATENT DOCUMENTS

| 4,816,567 | A | 3/1989 | Cabilly et al. |
| 5,225,539 | A | 7/1993 | Winter |
| 7,657,380 | B2 | 2/2010 | Lazar et al. |
| 2007/0048785 | A1 | 3/2007 | Lin et al. |
| 2009/0142261 | A1 | 6/2009 | Hsu et al. |
| 2009/0169547 | A1 | 7/2009 | Sahin et al. |
| 2010/0261620 | A1 | 10/2010 | Almagro et al. |
| 2011/0059093 | A1 | 3/2011 | Hohmann et al. |
| 2011/0077224 | A1 | 3/2011 | Pandey et al. |
| 2011/0092372 | A1 | 4/2011 | Almagro et al. |
| 2011/0118299 | A1 | 5/2011 | Lovell et al. |
| 2011/0143443 | A9 | 6/2011 | Mercken et al. |
| 2012/0087861 | A1 | 4/2012 | Nitsch et al. |
| 2012/0276009 | A1 | 11/2012 | Pfeifer et al. |

FOREIGN PATENT DOCUMENTS

| WO | WO 92/01047 A1 | 1/1992 |
| WO | WO 93/08302 A1 | 4/1993 |
| WO | WO 95/17429 A1 | 8/1995 |
| WO | WO 96/04309 A1 | 2/1998 |
| WO | WO 04/006955 A1 | 1/2004 |
| WO | WO 2009/017161 A1 | 2/2009 |
| WO | WO 2010/144711 A1 | 12/2010 |

OTHER PUBLICATIONS

Brunden, et al. "Advances in tau-focused drug discovery for Alzheimer's disease and related tauopathies", *Nat Rev Drug Discov* 8:783-93, (2009).
Chai, et al. "Molecular Bases of Disease: Passive Immunization with Anti-Tau Antibodies in Two Transgenic Models: Reduction of Tau Pathology and Delay of Disease Progression", *J Biol Chem* 286:34457-67, (2011).
Boutajangout, et al. "Passive immunization targeting pathological phospho-tau protein in a mouse model reduces functional decline in clers tau aggregates from the brain" *J Neurochem* 118:658-67, (2011).
Boutajangout, et al. "Immunotherapy Targeting Pathological Tau Prevents Cognitive Declin in a New Tangle Mouse model", *J Neurosci* 30:16559-66, (2010).
Asuni, et al., "Immunotherapy Targeting Pathological Tau Conformers in a Tangle Mouse Model Reduces Brain Pathology with Associated Functional Improvements", J Neurosci 27:9115-29, (2007).
Frost, et al., "Protein Structure and Folding:Propagation of Tan Misfolding from the Outside to th eInside of a Cell", *J Biol Chem* 284:12845-52, (2009).
Clavaguera, et al. "Transmission and spreading of tauopathy in transgenic mouse brain", *Nat Cell Biol* 11:909-13 (2009).
Wu and Kabat, "An Analysis of the Sequences of the Variable Regions of Bence Jones Proteins and Myeloma Light Chains and Their Implications for Anti-Body Comlementarity", *J Exp Med* 132:211-50, (1970).
Chothia and Lesk, "Canonical Structures for the Hypervariable Regions of Immunoglobulins", *J Mol Biol* 196:901-17, (1987).
Abhinandan and Martin, "Analysis and improvements to Kabat and structurally correct numbering of antibody variable domains", *Mol Immunol* 45:3832-9 (2008).
Lefranc, et al. , "IMGT unique numbering for immunoglobulin and T cell receptor variable domains and Ig superfamily V-like domains", *Dev Comp Immunol* 27:55-77 (2003).
Almagro, J.C., "Identification of differences in the specificity-determining residues of antibodies that recognize antigens of different size:implications ofr the rational design of antibody repertoires", *J Mol Recognit* 17:132-43, (2004).

(Continued)

*Primary Examiner* — Adam Weidner

(57) ABSTRACT

The present invention relates to anti-PHF-tau antibodies and methods of making and using them.

18 Claims, 10 Drawing Sheets

(56) References Cited

OTHER PUBLICATIONS

Hanger, et al. "Tau phosphorylatiouthe therapeutic challenge for neurodegenerative disease", *Trends Mol Med* 15:112-9 (2009).

Wischik, et al. "Structural characterization of the core of the paired helical filament of Alzheimer disease", *Proc Natl Acad Sci U S A* 85:4884-8 (1988).

Mercken, et al., "Affinity Purification of Human $_T$ Proteins and the Construction of a Sensitive Sandwich Enzyme-Linked Immunosorbent Assay for Human $_T$ Detection", *J Neurochem* 58:548-53, (1992).

Kohler and Milstein, "Continuous cultures of fused cells secreting antibody of predefined specificity", *Nature* 256:495-7 (1975).

Singer, D., et al., "Neighbored phosphorylation sites as PHF-tau specific markers in Alzheimer's disease", Biochemical and Biophysical Research Communications, Academic Press Inc., US, vol. 346, No. 3, pp. 819-828, Aug. 4, 2006.

Porzig, R. et al., Epitope mapping of mAbs AT8 and Tau5 directed against hyperphosphorylated regions of the human tau protein:, Biochemical and Biophysical Research Communications, Academic Press Inc>, US, vol. 358, No. 2, pp. 644-649, Jun. 29, 2007.

Petry, Franck et al., "Specificity of Anti-Tau Antibodies when Analyzing Mice Models of Alzheimer's Disease: Problems and Solutions", PLOS ONE, vol. 9, No. 5, May 2, 2014, p. e94251.

Hoffmann, R. et al., "Unique Alzheimer's disease paired helical filament specific epitopes involve double phosphorylation at specific sites", Biochemistry, American Chemical Society, US, vol. 36, No. 26, pp. 8114-8124, Jul. 1, 1997.

Jicha, G., et al., "A conformation-and phosphorylation-dependent antibody recognizing the paired helical filaments of Alzheimer's disease", Journal of Neurochemistry, vol. 60, No. 5, pp. 2087-2095, 1997.

Lonberg, et al. , "Antigen=specific human antibodies from mice comprising four distinct genetic modifications", *Nature* 368:856-9, (1994).

Fishwild, et al., "High-avidity human IgGk monoclonal antibodies from a novel strain of minilocus transgenic mice", *Nat Biotechnol* 14:845-51 (1996).

Mendez, et al., *"Functional transplant of megabase human immunoglobulin loci recapitulates human antibody response in mice"*, *Nat Genet* 15:146-56 (1997).

Knappik, et al. "Fully Synthetic Human Combinatorial Antibody Libraries (HuCAL) Based on Modular Consensus Frameworks and CDRs Randomized with Trinucleotides", *J Mol Biol* 296:57-86 (2000).

Krebs, et al. "High-throughput generation and engineering of recombinant human antibodies", *J Immunol Methods* 254:67-84 (2001).

Shi, et al. "De Novo Selection of High-Affinity Antibodies from Synthetic Fab Libraries Displayed on Phase as pIX Fusion Proteins", *J Mol Biol* 397:385-96 (2010).

Padlan. E., "A Possible Procedure for Reducing the Inununogenicity of antibody Variable Domains While Preserving Their Ligand-Binding Properties", *Mol. Immunol.* 28:489-98 (1991).

Queen, et al. "A humanized antibody that binds to the interleukin 2 receptor", *Proc Natl Acad Sci U S A* 86:10029-33 (1989).

Greenberg and Davies, "A preparation of Alzheimer paired helical filaments that displays distinct τ proteins by polyacrylamide gel electrophoresis", *Proc Natl Acad Sci U S A* 87:5827-31 (1990).

Spillantini and Goedert, "Tau protein pathology in neurodegenerative diseases", *Trends Neurosci* 21:428-33 (1998).

Strohl,, "Optimization of Fc-mediated effector functions of monoclonal antibodies", *Curr Opin Biotechnol* 20:685-91 (2009).

Knight, et al. "Pharmacodynamic enhancement of the anti-platelet antibody Fab abciximab by site-specific pegylation", *Platelets* 15:409-18 (2004).

Leong, et al. , "Adapting Pharmacokinetic Properties of a Humanized Anti-interleukin-8 Antibody for Therapeutic Applications Using Site-Specific Pegylation", *Cytokine* 16:106-19 (2001).

Yang, et al., "Tailoring structure-function and pharmacokinetic properties of single-chain Fv proteins by site-specific PEGylation", *Protein Eng* 16:761-70 (2003).

Morris, et al. "The Many Faces of Tau"*Neuron* 70:410-26 (2011).

Mercken et al., Monoclonal antibodies with selective specificity for Alzheimer Tau are directed against phosphatase-sensitive epitopes. *Acta Neuropathol*, 84(3):265-272 (1992).

Brion, Jean-Pierre et al., "Neurofilament Monoclonal Antibodies RT97 and 8D8 Recognize Different Modified Epitopes in Paired Helical Filament—? In Alzheimer's Disease", Journal of Neurochemistry, vol. 60, No. 4, pp. 1372-1382, Apr. 1, 1993.

Hasegawa, Masato et al., "Characterization of Two Distinct Monocolonal Antibodies to Paired Helical Filaments: Further Evidence for Fetal-Type Phosphorylation of the? In Paired Helical Filaments", Journal of Neurochemistry, vol. 60, No. 6, pp. 2068-2077, Jun. 1, 1993.

Goedert, M. et al., "Epitope Mapping of Monoclonal Antibodies to the Paired Helical Filaments of Alzheimer's Disease:Identification of Phosphorylationsites in Tau Protein", Biochemical Journal, Portland Press LTD, GB., vol. 301, No. Part 03, p. 871-877, Aug. 1, 1994.

Condamines, O. et al., "New immunoassay for the mapping of neurofibrillary degeneration in Alzheimer's disease using two monoclonal antibodies against human paired helical filament tau proteins", Neuroscience Letters, Limerick, IE, vol. 192, No. 2, pp. 81-84, Jun. 9, 1995.

Hasegawa, M et al., "Characterization of MAB AP422, A Novel Phosphorylation-Dependent Monoclonal Antibody Against Tau Protein", FEBS Letters, Elsevier, Amsterdam, NL, vol. 384, pp. 25-30, Jan. 1, 1996.

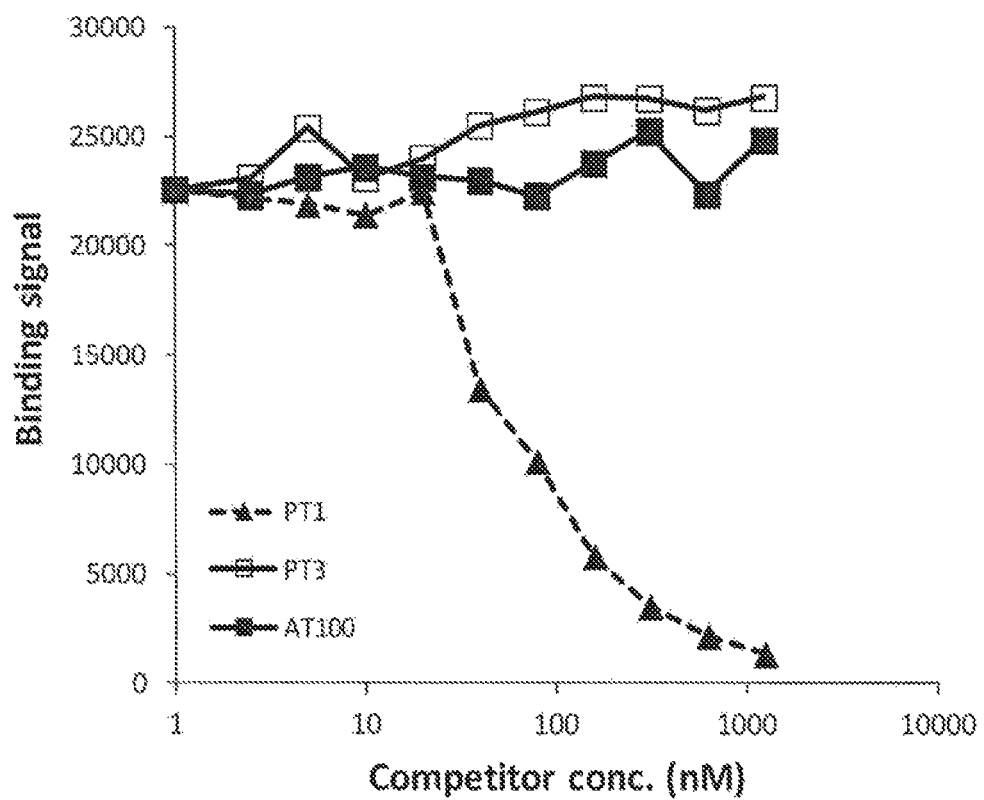

```
                           SEQUENCE LISTING

<160> NUMBER OF SEQ ID NOS: 39

<210> SEQ ID NO 1
<211> LENGTH: 352
<212> TYPE: PRT
<213> ORGANISM: Homo sapiens

<400> SEQUENCE: 1

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Ala Glu Glu Ala
            35                  40                  45

Gly Ile Gly Asp Thr Pro Ser Leu Glu Asp Glu Ala Ala Gly His Val
        50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
                100                 105                 110

Ile Pro Ala Lys Thr Pro Ala Pro Lys Thr Pro Pro Ser Ser Gly
                115                 120                 125

Glu Pro Pro Lys Ser Gly Asp Arg Ser Gly Tyr Ser Ser Pro Gly Ser
        130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
                180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Val Tyr Lys Pro Val
    210                 215                 220

Asp Leu Ser Lys Val Thr Ser Lys Cys Gly Ser Leu Gly Asn Ile His
225                 230                 235                 240

His Lys Pro Gly Gly Gly Gln Val Glu Val Lys Ser Glu Lys Leu Asp
                245                 250                 255

Phe Lys Asp Arg Val Gln Ser Lys Ile Gly Ser Leu Asp Asn Ile Thr
                260                 265                 270

His Val Pro Gly Gly Gly Asn Lys Lys Ile Glu Thr His Lys Leu Thr
            275                 280                 285

Phe Arg Glu Asn Ala Lys Ala Lys Thr Asp His Gly Ala Glu Ile Val
        290                 295                 300

Tyr Lys Ser Pro Val Val Ser Gly Asp Thr Ser Pro Arg His Leu Ser
305                 310                 315                 320

Asn Val Ser Ser Thr Gly Ser Ile Asp Met Val Asp Ser Pro Gln Leu
                325                 330                 335

Ala Thr Leu Ala Asp Glu Val Ser Ala Ser Leu Ala Lys Gln Gly Leu
                340                 345                 350
```

```
<210> SEQ ID NO 2
<211> LENGTH: 381
<212> TYPE: PRT
<213> ORGANISM: Homo sapiens

<400> SEQUENCE: 2

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Ala Glu Glu Ala Gly Ile Gly
65                  70                  75                  80

Asp Thr Pro Ser Leu Glu Asp Glu Ala Ala Gly His Val Thr Gln Ala
                85                  90                  95

Arg Met Val Ser Lys Ser Lys Asp Gly Thr Gly Ser Asp Asp Lys Lys
            100                 105                 110

Ala Lys Gly Ala Asp Gly Lys Thr Lys Ile Ala Thr Pro Arg Gly Ala
        115                 120                 125

Ala Pro Pro Gly Gln Lys Gly Gln Ala Asn Ala Thr Arg Ile Pro Ala
    130                 135                 140

Lys Thr Pro Pro Ala Pro Lys Thr Pro Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Pro Thr Arg
            180                 185                 190

Glu Pro Lys Lys Val Ala Val Val Arg Thr Pro Pro Lys Ser Pro Ser
        195                 200                 205

Ser Ala Lys Ser Arg Leu Gln Thr Ala Pro Val Pro Met Pro Asp Leu
    210                 215                 220

Lys Asn Val Lys Ser Lys Ile Gly Ser Thr Glu Asn Leu Lys His Gln
225                 230                 235                 240

Pro Gly Gly Gly Lys Val Gln Ile Val Tyr Lys Pro Val Asp Leu Ser
                245                 250                 255

Lys Val Thr Ser Lys Cys Gly Ser Leu Gly Asn Ile His His Lys Pro
            260                 265                 270

Gly Gly Gly Gln Val Glu Val Lys Ser Glu Lys Leu Asp Phe Lys Asp
        275                 280                 285

Arg Val Gln Ser Lys Ile Gly Ser Leu Asp Asn Ile Thr His Val Pro
    290                 295                 300

Gly Gly Gly Asn Lys Lys Ile Glu Thr His Lys Leu Thr Phe Arg Glu
305                 310                 315                 320

Asn Ala Lys Ala Lys Thr Asp His Gly Ala Glu Ile Val Tyr Lys Ser
                325                 330                 335

Pro Val Val Ser Gly Asp Thr Ser Pro Arg His Leu Ser Asn Val Ser
            340                 345                 350

Ser Thr Gly Ser Ile Asp Met Val Asp Ser Pro Gln Leu Ala Thr Leu
        355                 360                 365

Ala Asp Glu Val Ser Ala Ser Leu Ala Lys Gln Gly Leu
    370                 375                 380
```

```
<210> SEQ ID NO 3
<211> LENGTH: 410
<212> TYPE: PRT
<213> ORGANISM: Homo sapiens

<400> SEQUENCE: 3
```

| Met | Ala | Glu | Pro | Arg | Gln | Glu | Phe | Glu | Val | Met | Glu | Asp | His | Ala | Gly |
|---|---|---|---|---|---|---|---|---|---|---|---|---|---|---|---|
| 1 | | | | 5 | | | | | 10 | | | | | 15 | |

| Thr | Tyr | Gly | Leu | Gly | Asp | Arg | Lys | Asp | Gln | Gly | Gly | Tyr | Thr | Met | His |
|---|---|---|---|---|---|---|---|---|---|---|---|---|---|---|---|
| | | | 20 | | | | | 25 | | | | | 30 | | |

| Gln | Asp | Gln | Glu | Gly | Asp | Thr | Asp | Ala | Gly | Leu | Lys | Glu | Ser | Pro | Leu |
|---|---|---|---|---|---|---|---|---|---|---|---|---|---|---|---|
| | | 35 | | | | | 40 | | | | | 45 | | | |

| Gln | Thr | Pro | Thr | Glu | Asp | Gly | Ser | Glu | Glu | Pro | Gly | Ser | Glu | Thr | Ser |
|---|---|---|---|---|---|---|---|---|---|---|---|---|---|---|---|
| | 50 | | | | | 55 | | | | | 60 | | | | |

| Asp | Ala | Lys | Ser | Thr | Pro | Thr | Ala | Glu | Asp | Val | Thr | Ala | Pro | Leu | Val |
|---|---|---|---|---|---|---|---|---|---|---|---|---|---|---|---|
| 65 | | | | | 70 | | | | | 75 | | | | | 80 |

| Asp | Glu | Gly | Ala | Pro | Gly | Lys | Gln | Ala | Ala | Gln | Pro | His | Thr | Glu |
|---|---|---|---|---|---|---|---|---|---|---|---|---|---|---|
| | | | | 85 | | | | | 90 | | | | | 95 |

| Ile | Pro | Glu | Gly | Thr | Thr | Ala | Glu | Glu | Ala | Gly | Ile | Gly | Asp | Thr | Pro |
|---|---|---|---|---|---|---|---|---|---|---|---|---|---|---|---|
| | | | | 100 | | | | | 105 | | | | | 110 | |

| Ser | Leu | Glu | Asp | Glu | Ala | Ala | Gly | His | Val | Thr | Gln | Ala | Arg | Met | Val |
|---|---|---|---|---|---|---|---|---|---|---|---|---|---|---|---|
| | | | 115 | | | | | 120 | | | | | 125 | | |

| Ser | Lys | Ser | Lys | Asp | Gly | Thr | Gly | Ser | Asp | Asp | Lys | Lys | Ala | Lys | Gly |
|---|---|---|---|---|---|---|---|---|---|---|---|---|---|---|---|
| | 130 | | | | | 135 | | | | | 140 | | | | |

| Ala | Asp | Gly | Lys | Thr | Lys | Ile | Ala | Thr | Pro | Arg | Gly | Ala | Ala | Pro | Pro |
|---|---|---|---|---|---|---|---|---|---|---|---|---|---|---|---|
| 145 | | | | | 150 | | | | | 155 | | | | | 160 |

| Gly | Gln | Lys | Gly | Gln | Ala | Asn | Ala | Thr | Arg | Ile | Pro | Ala | Lys | Thr | Pro |
|---|---|---|---|---|---|---|---|---|---|---|---|---|---|---|---|
| | | | | 165 | | | | | 170 | | | | | 175 | |

| Pro | Ala | Pro | Lys | Thr | Pro | Pro | Ser | Ser | Gly | Glu | Pro | Pro | Lys | Ser | Gly |
|---|---|---|---|---|---|---|---|---|---|---|---|---|---|---|---|
| | | | 180 | | | | | 185 | | | | | 190 | | |

| Asp | Arg | Ser | Gly | Tyr | Ser | Ser | Pro | Gly | Ser | Pro | Gly | Thr | Pro | Gly | Ser |
|---|---|---|---|---|---|---|---|---|---|---|---|---|---|---|---|
| | | 195 | | | | | 200 | | | | | 205 | | | |

| Arg | Ser | Arg | Thr | Pro | Ser | Leu | Pro | Thr | Pro | Pro | Thr | Arg | Glu | Pro | Lys |
|---|---|---|---|---|---|---|---|---|---|---|---|---|---|---|---|
| | 210 | | | | | 215 | | | | | 220 | | | | |

| Lys | Val | Ala | Val | Arg | Thr | Pro | Pro | Lys | Ser | Pro | Ser | Ser | Ala | Lys |
|---|---|---|---|---|---|---|---|---|---|---|---|---|---|---|
| 225 | | | | | 230 | | | | | 235 | | | | | 240 |

| Ser | Arg | Leu | Gln | Thr | Ala | Pro | Val | Pro | Met | Pro | Asp | Leu | Lys | Asn | Val |
|---|---|---|---|---|---|---|---|---|---|---|---|---|---|---|---|
| | | | | 245 | | | | | 250 | | | | | 255 | |

| Lys | Ser | Lys | Ile | Gly | Ser | Thr | Glu | Asn | Leu | Lys | His | Gln | Pro | Gly | Gly |
|---|---|---|---|---|---|---|---|---|---|---|---|---|---|---|---|
| | | | 260 | | | | | 265 | | | | | 270 | | |

| Gly | Lys | Val | Gln | Ile | Val | Tyr | Lys | Pro | Val | Asp | Leu | Ser | Lys | Val | Thr |
|---|---|---|---|---|---|---|---|---|---|---|---|---|---|---|---|
| | | 275 | | | | | 280 | | | | | 285 | | | |

| Ser | Lys | Cys | Gly | Ser | Leu | Gly | Asn | Ile | His | His | Lys | Pro | Gly | Gly | Gly |
|---|---|---|---|---|---|---|---|---|---|---|---|---|---|---|---|
| | 290 | | | | | 295 | | | | | 300 | | | | |

| Gln | Val | Glu | Val | Lys | Ser | Glu | Lys | Leu | Asp | Phe | Lys | Asp | Arg | Val | Gln |
|---|---|---|---|---|---|---|---|---|---|---|---|---|---|---|---|
| 305 | | | | | 310 | | | | | 315 | | | | | 320 |

| Ser | Lys | Ile | Gly | Ser | Leu | Asp | Asn | Ile | Thr | His | Val | Pro | Gly | Gly | Gly |
|---|---|---|---|---|---|---|---|---|---|---|---|---|---|---|---|
| | | | | 325 | | | | | 330 | | | | | 335 | |

| Asn | Lys | Lys | Ile | Glu | Thr | His | Lys | Leu | Thr | Phe | Arg | Glu | Asn | Ala | Lys |
|---|---|---|---|---|---|---|---|---|---|---|---|---|---|---|---|
| | | | 340 | | | | | 345 | | | | | 350 | | |

| Ala | Lys | Thr | Asp | His | Gly | Ala | Glu | Ile | Val | Tyr | Lys | Ser | Pro | Val | Val |
|---|---|---|---|---|---|---|---|---|---|---|---|---|---|---|---|
| | | 355 | | | | | 360 | | | | | 365 | | | |

| Ser | Gly | Asp | Thr | Ser | Pro | Arg | His | Leu | Ser | Asn | Val | Ser | Thr | Gly |
|---|---|---|---|---|---|---|---|---|---|---|---|---|---|---|
| | 370 | | | | | 375 | | | | | 380 | | | | |

Ser Ile Asp Met Val Asp Ser Pro Gln Leu Ala Thr Leu Ala Asp Glu
385                 390                 395                 400

Val Ser Ala Ser Leu Ala Lys Gln Gly Leu
            405                 410

<210> SEQ ID NO 4
<211> LENGTH: 383
<212> TYPE: PRT
<213> ORGANISM: Homo sapiens

<400> SEQUENCE: 4

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
    130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Ile Asn Lys Lys Leu
    210                 215                 220

Asp Leu Ser Asn Val Gln Ser Lys Cys Gly Ser Lys Asp Asn Ile Lys
225                 230                 235                 240

His Val Pro Gly Gly Gly Ser Val Gln Ile Val Tyr Lys Pro Val Asp
                245                 250                 255

Leu Ser Lys Val Thr Ser Lys Cys Gly Ser Leu Gly Asn Ile His His
            260                 265                 270

Lys Pro Gly Gly Gly Gln Val Glu Val Lys Ser Glu Lys Leu Asp Phe
        275                 280                 285

Lys Asp Arg Val Gln Ser Lys Ile Gly Ser Leu Asp Asn Ile Thr His
    290                 295                 300

Val Pro Gly Gly Gly Asn Lys Lys Ile Glu Thr His Lys Leu Thr Phe
305                 310                 315                 320

Arg Glu Asn Ala Lys Ala Lys Thr Asp His Gly Ala Glu Ile Val Tyr
                325                 330                 335

Lys Ser Pro Val Val Ser Gly Asp Thr Ser Pro Arg His Leu Ser Asn
            340                 345                 350

Val Ser Ser Thr Gly Ser Ile Asp Met Val Asp Ser Pro Gln Leu Ala
    355                 360                 365

Thr Leu Ala Asp Glu Val Ser Ala Ser Leu Ala Lys Gln Gly Leu
    370                 375                 380

<210> SEQ ID NO 5
<211> LENGTH: 441
<212> TYPE: PRT
<213> ORGANISM: Homo sapiens

<400> SEQUENCE: 5

Met Ala Glu Pro Arg Gln Glu Phe Glu Val Met Glu Asp His Ala Gly
 1               5                  10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Asn
            355                 360                 365

Lys Lys Ile Glu Thr His Lys Leu Thr Phe Arg Glu Asn Ala Lys Ala
    370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
                420                 425                 430

Ser Ala Ser Leu Ala Lys Gln Gly Leu
            435                 440

<210> SEQ ID NO 6
<211> LENGTH: 441
<212> TYPE: PRT
<213> ORGANISM: Homo sapiens

<400> SEQUENCE: 6

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
        50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

```
Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
                340                 345                 350

Lys Ile Gly Ser Leu Asp Asn Ile Thr His Val Pro Gly Gly Gly Asn
            355                 360                 365

Lys Lys Ile Glu Thr His Lys Leu Thr Phe Arg Glu Asn Ala Lys Ala
        370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Thr Gly Ser
                405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
                435                 440

<210> SEQ ID NO 7
<211> LENGTH: 5
<212> TYPE: PRT
<213> ORGANISM: Mus musculus

<400> SEQUENCE: 7

Ser Ser Trp Met Gly
1               5

<210> SEQ ID NO 8
<211> LENGTH: 17
<212> TYPE: PRT
<213> ORGANISM: Mus musculus

<400> SEQUENCE: 8

Asp Ile Leu Pro Gly Ser Gly Gly Thr Asn Tyr Asn Glu Arg Phe Lys
1               5                   10                  15

Gly

<210> SEQ ID NO 9
<211> LENGTH: 10
<212> TYPE: PRT
<213> ORGANISM: Mus musculus

<400> SEQUENCE: 9

Ser Tyr Tyr Asp Tyr Asp Arg Phe Ala Asn
1               5                   10

<210> SEQ ID NO 10
<211> LENGTH: 16
<212> TYPE: PRT
<213> ORGANISM: Mus musculus

<400> SEQUENCE: 10

Arg Ser Ser Glu Ser Leu Leu His Ser Asn Gly Asn Thr Tyr Leu Tyr
1               5                   10                  15
```

```
<210> SEQ ID NO 11
<211> LENGTH: 7
<212> TYPE: PRT
<213> ORGANISM: Mus musculus

<400> SEQUENCE: 11

Arg Met Ser Asn Leu Ala Ser
1               5

<210> SEQ ID NO 12
<211> LENGTH: 9
<212> TYPE: PRT
<213> ORGANISM: Mus musculus

<400> SEQUENCE: 12

Met Gln Tyr Leu Glu Tyr Pro Leu Thr
1               5

<210> SEQ ID NO 13
<211> LENGTH: 5
<212> TYPE: PRT
<213> ORGANISM: Mus musculus

<400> SEQUENCE: 13

Ser Tyr Ala Met Ser
1               5

<210> SEQ ID NO 14
<211> LENGTH: 16
<212> TYPE: PRT
<213> ORGANISM: Mus musculus

<400> SEQUENCE: 14

Ser Ile Ser Lys Gly Gly Asn Thr Tyr Tyr Pro Asn Ser Val Lys Gly
1               5                   10                  15

<210> SEQ ID NO 15
<211> LENGTH: 10
<212> TYPE: PRT
<213> ORGANISM: Homo sapiens

<400> SEQUENCE: 15

Gly Trp Gly Asp Tyr Gly Trp Phe Ala Tyr
1               5                   10

<210> SEQ ID NO 16
<211> LENGTH: 11
<212> TYPE: PRT
<213> ORGANISM: Mus musculus

<400> SEQUENCE: 16

Lys Ala Ser Gln Asp Ile Asn Arg Tyr Leu Asn
1               5                   10

<210> SEQ ID NO 17
<211> LENGTH: 7
<212> TYPE: PRT
<213> ORGANISM: Mus musculus

<400> SEQUENCE: 17

Arg Ala Asn Arg Leu Leu Asp
1               5
```

```
<210> SEQ ID NO 18
<211> LENGTH: 9
<212> TYPE: PRT
<213> ORGANISM: Mus musculus

<400> SEQUENCE: 18

Leu Gln Tyr Asp Glu Phe Pro Leu Thr
1               5

<210> SEQ ID NO 19
<211> LENGTH: 7
<212> TYPE: PRT
<213> ORGANISM: Mus musculus

<400> SEQUENCE: 19

Gly Tyr Thr Phe Ser Ser Ser
1               5

<210> SEQ ID NO 20
<211> LENGTH: 6
<212> TYPE: PRT
<213> ORGANISM: Mus musculus

<400> SEQUENCE: 20

Leu Pro Gly Ser Gly Gly
1               5

<210> SEQ ID NO 21
<211> LENGTH: 9
<212> TYPE: PRT
<213> ORGANISM: Mus musculus

<400> SEQUENCE: 21

Ser Tyr Tyr Asp Tyr Asp Arg Phe Ala
1               5

<210> SEQ ID NO 22
<211> LENGTH: 12
<212> TYPE: PRT
<213> ORGANISM: Mus musculus

<400> SEQUENCE: 22

Ser Glu Ser Leu Leu His Ser Asn Gly Asn Thr Tyr
1               5                   10

<210> SEQ ID NO 23
<211> LENGTH: 3
<212> TYPE: PRT
<213> ORGANISM: Mus musculus

<400> SEQUENCE: 23

Arg Met Ser
1

<210> SEQ ID NO 24
<211> LENGTH: 6
<212> TYPE: PRT
<213> ORGANISM: Mus musculus

<400> SEQUENCE: 24

Tyr Leu Glu Tyr Pro Leu
1               5
```

```
<210> SEQ ID NO 25
<211> LENGTH: 7
<212> TYPE: PRT
<213> ORGANISM: Mus musculus

<400> SEQUENCE: 25

Gly Phe Thr Phe Ser Ser Tyr
1               5

<210> SEQ ID NO 26
<211> LENGTH: 5
<212> TYPE: PRT
<213> ORGANISM: Mus musculus

<400> SEQUENCE: 26

Ser Lys Gly Gly Asn
1               5

<210> SEQ ID NO 27
<211> LENGTH: 9
<212> TYPE: PRT
<213> ORGANISM: Mus musculus

<400> SEQUENCE: 27

Gly Trp Gly Asp Tyr Gly Trp Phe Ala
1               5

<210> SEQ ID NO 28
<211> LENGTH: 7
<212> TYPE: PRT
<213> ORGANISM: Mus musculus

<400> SEQUENCE: 28

Ser Gln Asp Ile Asn Arg Tyr
1               5

<210> SEQ ID NO 29
<211> LENGTH: 3
<212> TYPE: PRT
<213> ORGANISM: Mus musculus

<400> SEQUENCE: 29

Arg Ala Asn
1

<210> SEQ ID NO 30
<211> LENGTH: 6
<212> TYPE: PRT
<213> ORGANISM: Mus musculus

<400> SEQUENCE: 30

Tyr Asp Glu Phe Pro Leu
1               5

<210> SEQ ID NO 31
<211> LENGTH: 357
<212> TYPE: DNA
<213> ORGANISM: Mus musculus

<400> SEQUENCE: 31
caggttcagc tgcagcagtc tggaactgag ctgatgaagc ctggggcctc agtgaagata      60
tcctgcaagg ctactggcta cacattcagt agctcctgga tggggtgggt taagcagagg     120
cctggacatg gccttgagtg gattggagac attttacctg gaagtggtgg tactaactac     180
```

```
aatgagaggt tcaagggcaa ggcctcattc actgcagaaa catcctccaa cacagcctac      240
atgcaactca gcagcctgac atctgaggac tctgccgtct attactgtgt aagaagctac      300
tatgattacg accgctttgc taactggggc caagggactc tggtcactgt ctctgca        357
```

<210> SEQ ID NO 32
<211> LENGTH: 336
<212> TYPE: DNA
<213> ORGANISM: Mus musculus

<400> SEQUENCE: 32

```
gatattgtga tgactcaggc tgcaccctct gtacctgtca ctcctggaga gtcagtttcc       60
atctcctgca ggtctagtga gagtctcctg catagtaatg gcaacactta cttgtattgg      120
ttcctgcaga ggccaggcca gtctcctcag ctcctgatat atcggatgtc caaccttgcc      180
tcaggagtcc cagacaggtt cagtggcagt gggtcaggaa ctgctttcac actgagaatc      240
agtagagtgg aggctgagga tgtgggtgtt tattactgta tgcaatatct agaatatccg      300
ctcacgttcg gtgctgggac caagctggag ctgaaa                                336
```

<210> SEQ ID NO 33
<211> LENGTH: 354
<212> TYPE: DNA
<213> ORGANISM: Mus musculus

<400> SEQUENCE: 33

```
gaagtgaagc tggtggagtc tgggggagac ttagtgaagc ctggagggtc cctgaaactc       60
tcctgtgcag cctctggatt cactttcagt agctatgcca tgtcttgggt tcgccagaat      120
ccagagaaga ggctggagtg ggtcgcatcc attagtaagg gtggtaacac ctactatcca      180
aacagcgtga aggccgatt caccatctcc agagataatg ccaggaacat cctgtacctg      240
caaatgagca gtctgaggtc tgaggacacg gccctttatt actgtgcaag aggctggggt      300
gattacgggt ggtttgctta ctggggccaa gtgactctgg tcactgtctc tgca           354
```

<210> SEQ ID NO 34
<211> LENGTH: 321
<212> TYPE: DNA
<213> ORGANISM: Mus musculus

<400> SEQUENCE: 34

```
gacatcaaga tgacccagtc tccatcttcc atgtatgcat ctctaggaga gagagtcact       60
atcacttgca aggcgagtca ggacattaat aggtatttaa actggttcca gcagaaacca      120
gggaaatctc ctaagaccct gatctatcgt gcaaacagat tgctagatgg ggtcccatca      180
aggttcagtg gcagtggatc tgggcaagat tactctctca ccatcagcag cctggattat      240
gaagatatgg gaatttatta ttgtctacag tatgatgagt ttccgctcac gttcggtgat      300
gggaccaagc tggagctgaa a                                               321
```

<210> SEQ ID NO 35
<211> LENGTH: 119
<212> TYPE: PRT
<213> ORGANISM: Mus musculus

<400> SEQUENCE: 35

Gln Val Gln Leu Gln Gln Ser Gly Thr Glu Leu Met Lys Pro Gly Ala
1               5                  10                  15

Ser Val Lys Ile Ser Cys Lys Ala Thr Gly Tyr Thr Phe Ser Ser Ser
            20                  25                  30

```
Trp Met Gly Trp Val Lys Gln Arg Pro Gly His Gly Leu Glu Trp Ile
         35                  40                  45

Gly Asp Ile Leu Pro Gly Ser Gly Gly Thr Asn Tyr Asn Glu Arg Phe
 50                  55                  60

Lys Gly Lys Ala Ser Phe Thr Ala Glu Thr Ser Ser Asn Thr Ala Tyr
 65                  70                  75                  80

Met Gln Leu Ser Ser Leu Thr Ser Glu Asp Ser Ala Val Tyr Tyr Cys
                 85                  90                  95

Val Arg Ser Tyr Tyr Asp Tyr Asp Arg Phe Ala Asn Trp Gly Gln Gly
                100                 105                 110

Thr Leu Val Thr Val Ser Ala
        115
```

<210> SEQ ID NO 36
<211> LENGTH: 112
<212> TYPE: PRT
<213> ORGANISM: Mus musculus

<400> SEQUENCE: 36

```
Asp Ile Val Met Thr Gln Ala Ala Pro Ser Val Pro Val Thr Pro Gly
 1               5                  10                  15

Glu Ser Val Ser Ile Ser Cys Arg Ser Ser Glu Ser Leu Leu His Ser
                 20                  25                  30

Asn Gly Asn Thr Tyr Leu Tyr Trp Phe Leu Gln Arg Pro Gly Gln Ser
             35                  40                  45

Pro Gln Leu Leu Ile Tyr Arg Met Ser Asn Leu Ala Ser Gly Val Pro
 50                  55                  60

Asp Arg Phe Ser Gly Ser Gly Ser Gly Thr Ala Phe Thr Leu Arg Ile
 65                  70                  75                  80

Ser Arg Val Glu Ala Glu Asp Val Gly Val Tyr Tyr Cys Met Gln Tyr
                 85                  90                  95

Leu Glu Tyr Pro Leu Thr Phe Gly Ala Gly Thr Lys Leu Glu Leu Lys
                100                 105                 110
```

<210> SEQ ID NO 37
<211> LENGTH: 118
<212> TYPE: PRT
<213> ORGANISM: Mus musculus

<400> SEQUENCE: 37

```
Glu Val Lys Leu Val Glu Ser Gly Gly Asp Leu Val Lys Pro Gly Gly
 1               5                  10                  15

Ser Leu Lys Leu Ser Cys Ala Ala Ser Gly Phe Thr Phe Ser Ser Tyr
                 20                  25                  30

Ala Met Ser Trp Val Arg Gln Asn Pro Glu Lys Arg Leu Glu Trp Val
             35                  40                  45

Ala Ser Ile Ser Lys Gly Gly Asn Thr Tyr Tyr Pro Asn Ser Val Lys
 50                  55                  60

Gly Arg Phe Thr Ile Ser Arg Asp Asn Ala Arg Asn Ile Leu Tyr Leu
 65                  70                  75                  80

Gln Met Ser Ser Leu Arg Ser Glu Asp Thr Ala Leu Tyr Tyr Cys Ala
                 85                  90                  95

Arg Gly Trp Gly Asp Tyr Gly Trp Phe Ala Tyr Trp Gly Gln Val Thr
                100                 105                 110

Leu Val Thr Val Ser Ala
        115
```

```
<210> SEQ ID NO 38
<211> LENGTH: 107
<212> TYPE: PRT
<213> ORGANISM: Mus musculus

<400> SEQUENCE: 38

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Arg Tyr
            20                  25                  30

Leu Asn Trp Phe Gln Gln Lys Pro Gly Lys Ser Pro Lys Thr Leu Ile
        35                  40                  45

Tyr Arg Ala Asn Arg Leu Leu Asp Gly Val Pro Ser Arg Phe Ser Gly
    50                  55                  60

Ser Gly Ser Gly Gln Asp Tyr Ser Leu Thr Ile Ser Ser Leu Asp Tyr
65                  70                  75                  80

Glu Asp Met Gly Ile Tyr Tyr Cys Leu Gln Tyr Asp Glu Phe Pro Leu
                85                  90                  95

Thr Phe Gly Asp Gly Thr Lys Leu Glu Leu Lys
            100                 105

<210> SEQ ID NO 39
<211> LENGTH: 18
<212> TYPE: PRT
<213> ORGANISM: Artificial Sequence
<220> FEATURE:
<223> OTHER INFORMATION: phosphorylated tau peptide corresponding to
      residues 194-211 of control tau

<400> SEQUENCE: 39

Arg Ser Gly Tyr Ser Ser Pro Gly Ser Pro Gly Thr Pro Gly Ser Arg
1               5                   10                  15

Ser Arg
```

ANTI-PHF-TAU ANTIBODIES AND THEIR USES

This application is a continuation application of U.S. patent application Ser. No. 15/138,635, filed Apr. 26, 2016, which claims priority to Ser. No. 14/363,888, filed Jun. 9, 2014, U.S. Pat. No. 9,371,376, which is a 371 National Stage Application of PCT/US2012/070486, with an international filing date of Dec. 19, 2012, and claims the benefit of U.S. Provisional Application No. 61/577,817 filed Dec. 20, 2011.

FIELD OF THE INVENTION

The present invention relates to anti-PHF-tau antibodies, and methods of making and using them.

BACKGROUND OF THE INVENTION

Alzheimer's Disease (AD) is a degenerative brain disorder characterized clinically by progressive loss of memory, cognition, reasoning, judgment and emotional stability that gradually leads to profound mental deterioration and ultimately death. AD is a very common cause of progressive mental failure (dementia) in aged humans and is believed to represent the fourth most common medical cause of death in the United States. AD has been observed in ethnic groups worldwide and presents a major present and future public health problem.

The brains of individuals with AD exhibit characteristic lesions termed senile (or amyloid) plaques, amyloid angiopathy (amyloid deposits in blood vessels) and neurofibrillary tangles. Large numbers of these lesions, particularly amyloid plaques and neurofibrillary tangles of paired helical filaments, are generally found in several areas of the human brain important for memory and cognitive function in patients with AD.

The main protein component of the neurofibrillary degeneration in AD and several other neurodegenerative diseases is a hyperphosphorylated form of the microtubule associated protein tau. Developing therapeutics preventing or clearing tau aggregation has been of interest for many years but candidate drugs, including anti-aggregation compounds and kinase inhibitors, have only just entered in clinical testing (Brunden, et al. *Nat Rev Drug Discov* 8:783-93, 2009)

Recently, preclinical evidence has been produced in transgenic tau mouse models that active and passive immunization for tau can have therapeutic potential (Chai, et al. *J Biol Chem* 286:34457-67, 2011, Boutajangout, et al. *J Neurochem* 118:658-67, 2011, Boutajangout, et al. *J Neurosci* 30:16559-66, 2010, Asuni, et al. *J Neurosci* 27:9115-29, 2007). A tauopathy transmission and spreading hypothesis has recently been described and is based on the Braak stages of tauopathy progression in human brain and tauopathy spreading after tau aggregate injections in preclinical tau models (Frost et al. *J Biol Chem* 284:12845-52, 2009, Clavaguera, et al. *Nat Cell Biol* 11:909-13, 2009). Thus, there is a need for therapeutics to prevent tau aggregation and tauopathy progression to treat AD and other neurodegenerative diseases.

BRIEF DESCRIPTION OF THE FIGURES

FIGS. 2A-2B show competition of labeled PT1 by various anti-tau antibodies. (A) PT1, PT3 and AT100 and (B) AT8, PT2, PT4 and PT5.

SUMMARY OF THE INVENTION

Figure 1:
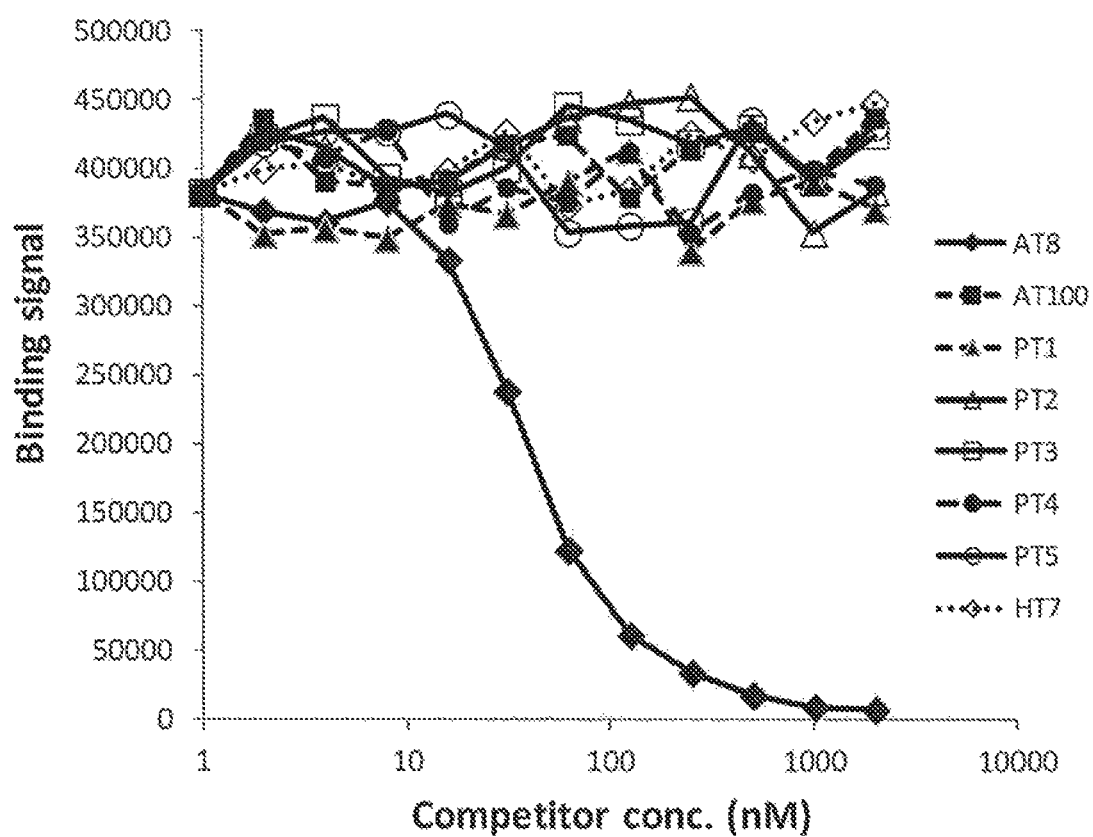
FIG. 1 shows competition of labeled AT8 by various anti-tau antibodies.
Figure 2B:
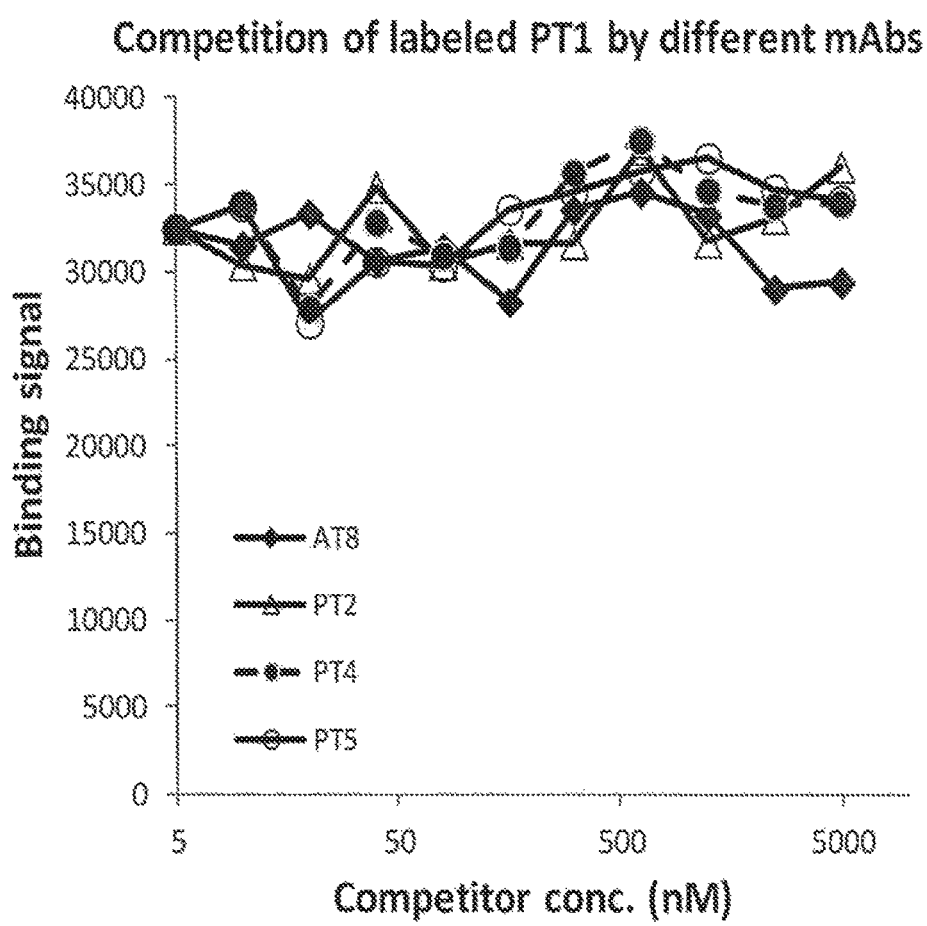
Figure 3A:
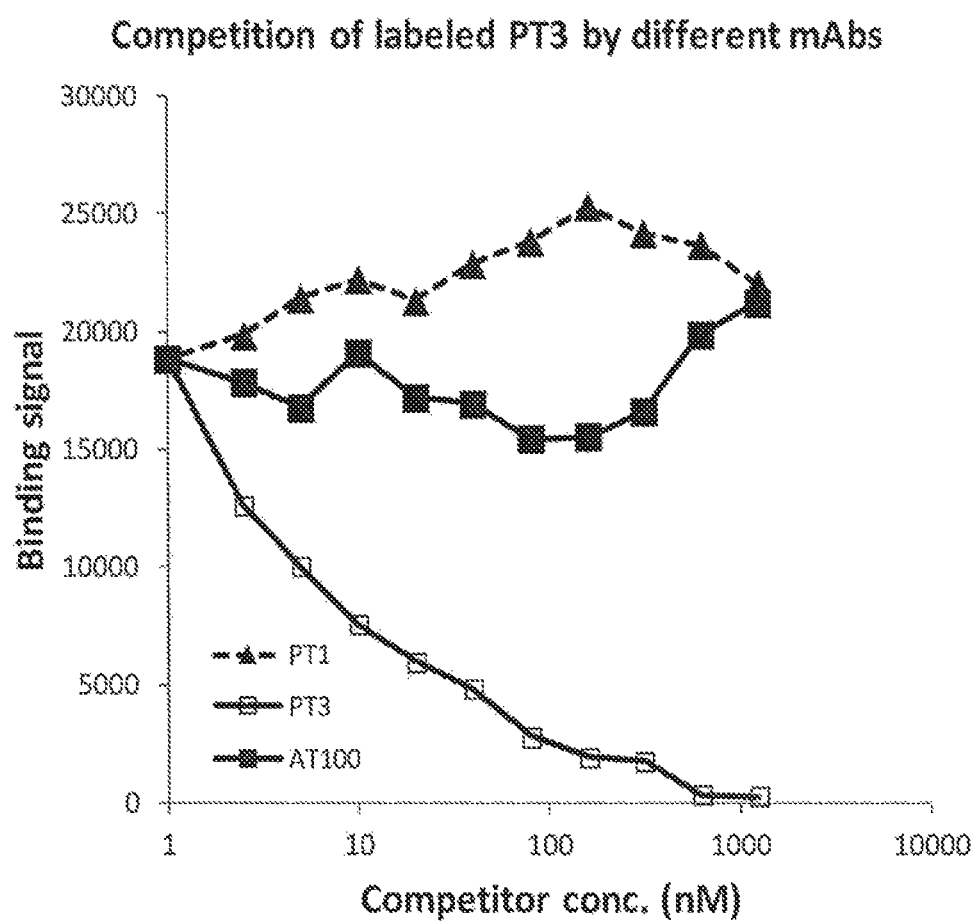
FIGS. 3A-3B show competition of labeled PT3 by various anti-tau antibodies. (A) PT1, PT3 and AT100 and (B) AT8, PT2, PT4 and PT5.
Figure 3B:
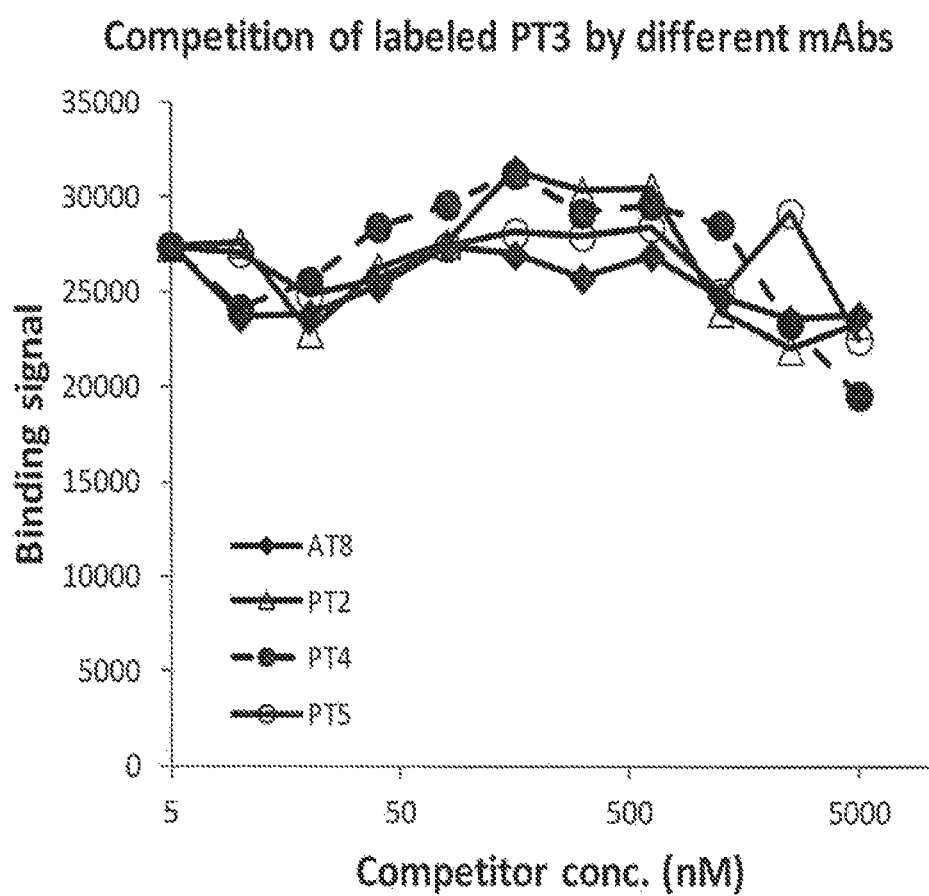
Figure 4:
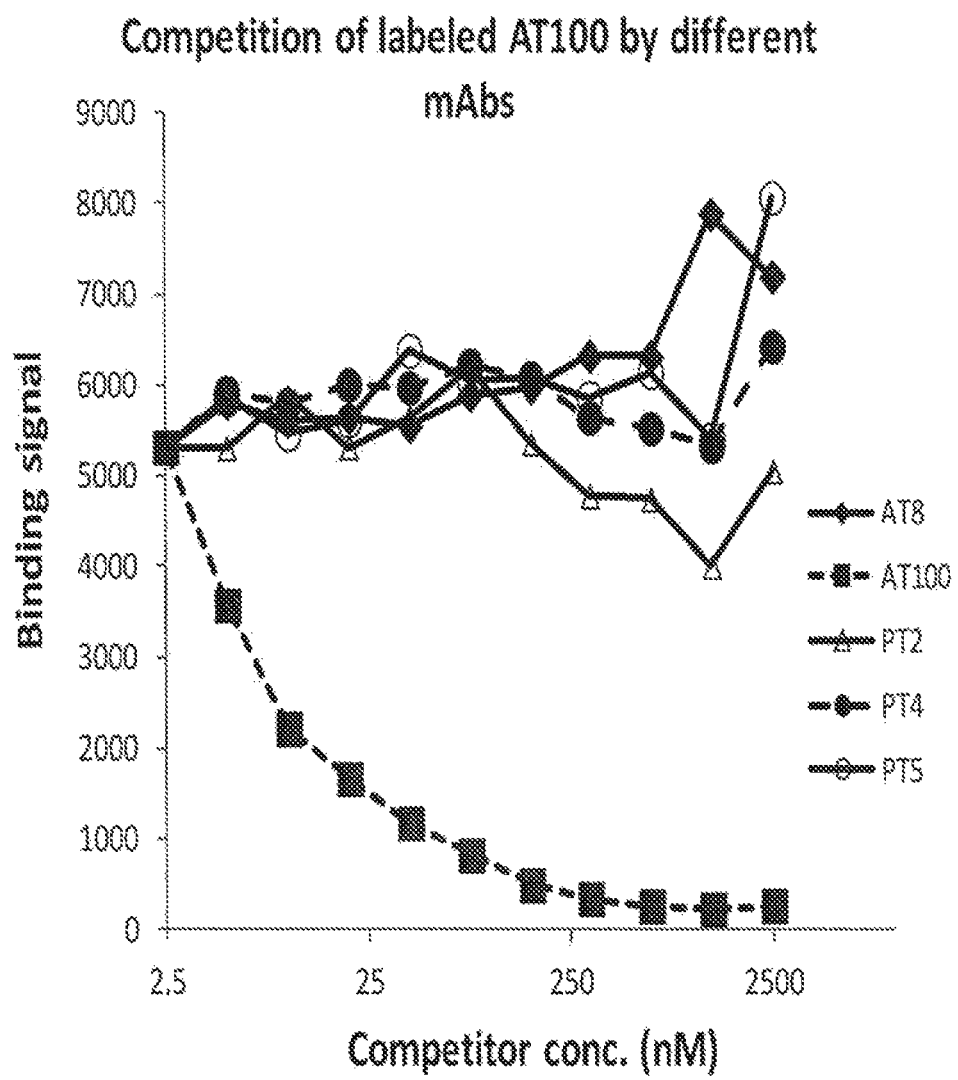
FIG. 4 shows competition of labeled AT100 by various anti-tau antibodies.
Figure 5:
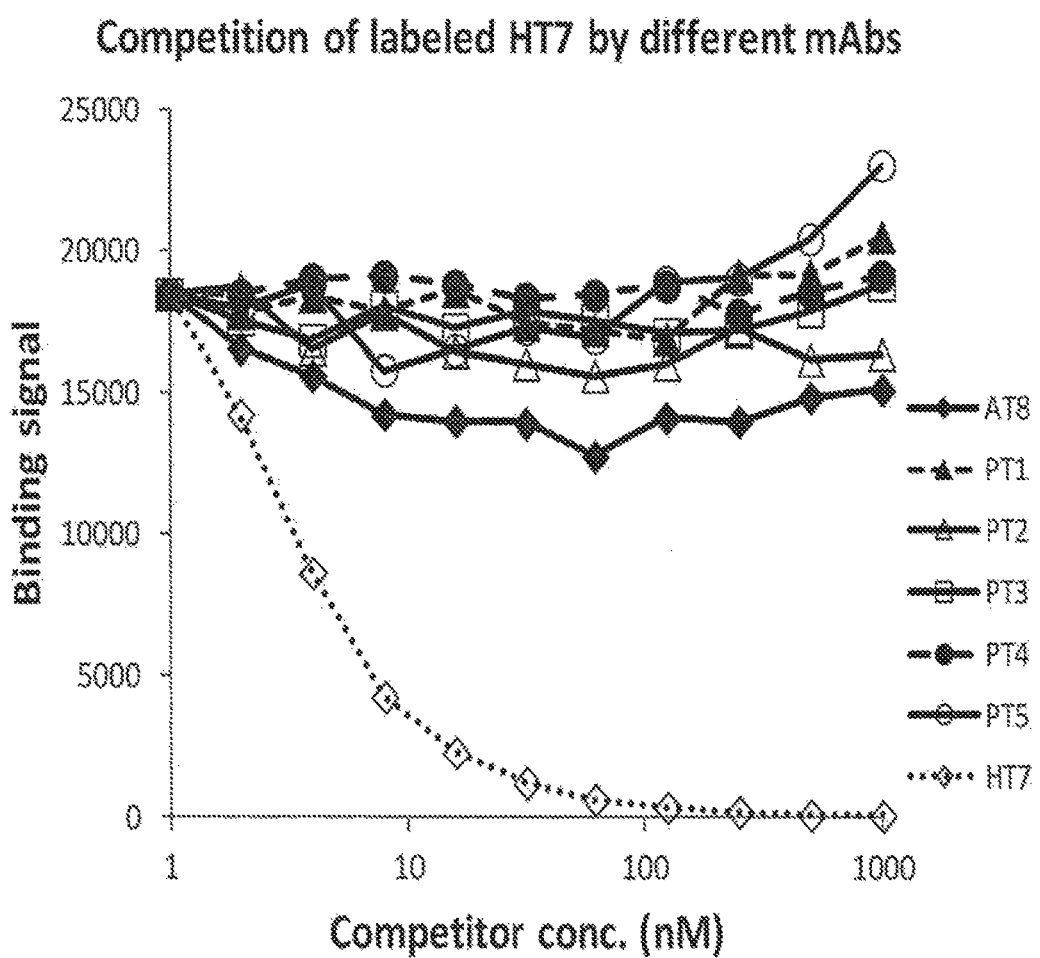
FIG. 5 shows competition of labeled HT7 by various anti-tau antibodies.

One aspect of the invention is an isolated antibody that binds PHF-tau comprising an antigen-binding site of a heavy chain variable region (VH) of SEQ ID NO:35 or 37, and an antigen-binding site of a light chain variable region (VL) of SEQ ID NO:36 or 38.

Another aspect of the invention is an isolated antibody that binds PHF-tau comprising certain heavy chain and light chain complementarity determining regions.

Another aspect of the invention is an isolated antibody that binds PHF-tau comprising an antigen-binding site of a VH of SEQ ID NO:35 and an antigen-binding site of a VL of SEQ ID NO: 36.

Another aspect of the invention is an isolated antibody that binds PHF-tau comprising an antigen-binding site of a VH of SEQ ID NO:37 and an antigen-binding site of a VL of SEQ ID NO: 38.

Another aspect of the invention is an isolated antibody or fragment that competes for PHF-tau binding with a monoclonal antibody comprising an antigen-binding site of a VH of SEQ ID NO: 35 and an antigen-binding site of a VL of SEQ ID NO: 36, or an antigen-binding site of a VH of SEQ ID NO: 37 and an antigen-binding site of a VL of SEQ ID NO: 38.

Another aspect of the invention is polynucleotides encoding the antibodies of the invention or fragments thereof.

Another aspect of the invention is a vector comprising the polynucleotides of the invention.

Another aspect of the invention is a host cell comprising the vector of the invention.

Another aspect of the invention is a method of making an antibody that binds PHF-tau comprising culturing the host cell of the invention and recovering the antibody produced by the host cell.

DETAILED DESCRIPTION OF THE INVENTION

The term "antibodies" as used herein is meant in a broad sense and includes immunoglobulin or antibody molecules including polyclonal antibodies, monoclonal antibodies including murine, human, human-adapted, humanized and chimeric monoclonal antibodies and antibody fragments.

In general, antibodies are proteins or peptide chains that exhibit binding specificity to a specific antigen. Antibody structures are well known Immunoglobulins can be assigned to five major classes, namely IgA, IgD, IgE, IgG and IgM, depending on the heavy chain constant domain amino acid sequence. IgA and IgG are further sub-classified as the isotypes IgA1, IgA2, IgG1, IgG2, IgG3 and IgG4. Antibody light chains of any vertebrate species can be assigned to one of two clearly distinct types, namely kappa (κ) and lambda (λ), based on the amino acid sequences of their constant domains.

The term "antibody fragments" means a portion of an intact antibody. Examples of antibody fragments include Fab, Fab', F(ab')$_2$ and Fv fragments, CDR, antigen-binding site, heavy or light chain variable region, diabodies, single chain antibody molecules and multispecific antibodies formed from at least two intact antibodies or fragments thereof.

An immunoglobulin light or heavy chain variable region consists of a "framework" region interrupted by "antigen-binding sites". The antigen-binding sites are defined using various terms as follows: (i) Complementarity Determining Regions (CDRs) are based on sequence variability (Wu and Kabat *J Exp Med* 132:211-50, 1970). Generally, the antigen-binding site has three CDRs in each variable region (HCDR1, HCDR2 and HCDR3 in heavy chain variable region (VH) and LCDR1, LCDR2 and LCDR3 in light chain variable region (VL)) (Kabat et al., Sequences of Proteins of Immunological Interest, 5th Ed. Public Health Service, National Institutes of Health, Bethesda, Md., 1991). (ii) The term "hypervariable region", "HVR", or "HV" refers to the regions of an antibody variable domain which are hyper-variable in structure as defined by Chothia and Lesk (Chothia and Lesk *J Mol Biol* 196:901-17, 1987). Generally, the antigen-binding site has three hypervariable regions in each VH (H1, H2, H3) and VL (L1, L2, L3). Chothia and Lesk refer to structurally conserved HVs as "canonical structures". Numbering systems as well as annotation of CDRs and HVs have recently been revised by Abhinandan and Martin (Abhinandan and Martin *Mol Immunol* 45:3832-9, 2008). (iii) Another definition of the regions that form the antigen-binding site has been proposed by Lefranc (Lefranc, et al. *Dev Comp Immunol* 27:55-77, 2003) based on the comparison of V domains from immunoglobulins and T-cell receptors. The International ImMunoGeneTics (IMGT) database (http:_//www_imgt_org) provides a standardized numbering and definition of these regions. The correspondence between CDRs, HVs and IMGT delineations is described in Lefranc et al., supra. (iv) The antigen-binding site can also be delineated based on Specificity Determining Residue Usage (SDRU) (Almagro *J Mol Recognit* 17:132-43, 2004), where Specificity Determining Residues (SDR), refers to amino acid residues of an immunoglobulin that are directly involved in antigen contact.

"Framework" or "framework sequence" are the remaining sequences within the variable region of an antibody other than those defined to be antigen-binding site sequences. Because the exact definition of an antigen-binding site can be determined by various delineations as described above, the exact framework sequence depends on the definition of the antigen-binding site.

The term "monoclonal antibody" (mAb) as used herein means an antibody (or antibody fragment) obtained from a population of substantially homogeneous antibodies. Monoclonal antibodies are highly specific, typically being directed against a single antigenic determinant.

The term "epitope" as used herein means a portion of an antigen to which an antibody specifically binds. Epitopes usually consist of chemically active (such as polar, non-polar or hydrophobic) surface groupings of moieties such as amino acids, phosphorylated amino acids or polysaccharide side chains and can have specific three-dimensional structural characteristics, as well as specific charge characteristics. An epitope can be linear in nature or can be a discontinuous epitope, e.g., a conformational epitope, which is formed by a spatial relationship between non-contiguous amino acids of an antigen rather than a linear series of amino acids. A conformational epitope includes epitopes resulting from folding of an antigen, where amino acids from differing portions of the linear sequence of the antigen come in close proximity in 3-dimensional space.

Tau is an abundant central and peripheral nervous system protein having multiple well known isoforms. In the human CNS, six major tau isoforms ranging in size from 352 to 441 exist due to alternative splicing (Hanger, et al. *Trends Mol Med* 15:112-9, 2009). These isoforms differ from each other by the regulated inclusion of 0-2 N-terminal inserts, and 3 or 4 tandemly arranged microtubule-binding repeats, and are referred to as 0N3R (SEQ ID NO:1), 1N3R (SEQ ID NO:2), 2N3R (SEQ ID NO:3), 0N4R (SEQ ID NO:4), 1N4R (SEQ ID NO:5) and 2N4R (SEQ ID NO:6). The term "control tau" as used herein refers to the tau isoform of SEQ ID NO:6 that is devoid of phosphorylation and other post-translational modifications.

Tau binds microtubules and regulates transport of cargo through cells, a process that can be modulated by tau phosphorylation. In AD and related disorders abnormal phosphorylation of tau is prevalent and thought to precede and/or trigger aggregation of tau into fibrils, termed paired helical filaments (PHF). The major constituent of PHF is hyperphosphorylated tau. The term "paired helical filament-tau" or "PHF-tau" as used herein refers to well known tau aggregates in paired helical filaments. Two major regions in PHF structure are evident in electron microscopy, the fuzzy coat and the core filament; the fuzzy coat being sensitive to proteolysis and located outside of the filaments, and the protease resistant core of filaments forming the backbone of PHFs (Wischik, et al. *Proc Natl Acad Sci USA* 85:4884-8, 1988).

"Antibodies that bind PHF-tau" as used herein refers to antibodies that bind PHF-tau as assessed on western blot. Typically, antibody binding to PHF-tau can be assessed after Coomassie stain of about 500 ng of PHF-tau after 1 hour blocking in 5% (w/v) nonfat dry milk (NFDM) TBS-T, 0.05% Tween-20. Antibodies that bind PHF-tau optionally do not bind control tau (SEQ ID NO:6) as measured by western blot when tested under antigen loading condition where both control tau and PHF-tau is detected equally by tau antibodies that have no preference for PHF-tau epitopes (e.g. antibody HT7, (ThermoScientific, Rockford, Ill.) (Mercken, et al. *J Neurochem* 58:548-53, 1992). Such exemplary antigen loading conditions are 500 ng PHF-tau and 200 ng control tau.

Conventional well known one and three-letter amino acid codes are used herein.

Compositions of Matter

The present invention relates to anti-PHF-tau antibodies and uses of such antibodies. Such anti-PHF-tau antibodies may have the properties of binding a phosphorylated epitope on PHF-tau or binding to a non-phosphorylated epitope on PHF-tau. Anti-PHF-tau antibodies may be useful as therapeutics, and as research or diagnostic reagents to detect PHF-tau in biological samples, for example in tissues or cells.

One embodiment of the invention is an isolated antibody that binds PHF-tau comprising an antigen-binding site of a heavy chain variable region (VH) of SEQ ID NO:35 or 37, or an antigen-binding site of a light chain variable region (VL) of SEQ ID NO:36 or 38. Table 1 shows antigen-binding site residues of exemplary antibodies of the invention defined according to Kabat or Chothia as well as exemplary heavy and light chain variable regions.

In another embodiment, the antigen-binding site of the VH of the antibodies of the invention comprises heavy chain complementarity determining regions (CDRs) 1 (HCDR1), 2 (HCDR2) and 3 (HCDR3) of SEQ ID NOs:7, 8 and 9 or 13, 14 and 15, respectively, or the antigen-binding site of the VL of the antibodies of the invention comprises light chain CDRs 1 (LCDR1), 2 (LCDR2) and 3 (LCDR3) of SEQ ID NOs:10, 11 and 12 or 16, 17 and 18, respectively.

Another embodiment of the invention is an isolated antibody that binds PHF-tau comprising an antigen-binding site of a heavy chain variable region (VH) of SEQ ID NO:35 or 37, and an antigen-binding site of a light chain variable region (VL) of SEQ ID NO:36 or 38.

In another embodiment, the antigen-binding site of the VH of the antibodies of the invention comprises heavy chain complementarity determining regions (CDRs) 1 (HCDR1), 2 (HCDR2) and 3 (HCDR3) of SEQ ID NOs:7, 8 and 9 or 13, 14 and 15, respectively, and the antigen-binding site of the VL of the antibodies of the invention comprises light chain CDRs 1 (LCDR1), 2 (LCDR2) and 3 (LCDR3) of SEQ ID NOs:10, 11 and 12 or 16, 17 and 18, respectively.

TABLE 1

| Sequence name | SEQ ID NO: | Sequence |
|---|---|---|
| PT1 HCDR1, Kabat | 7 | SSWMG |
| PT1 HCDR2, Kabat | 8 | DILPGSGGTNYNERFKG |
| PT1 HCDR3, Kabat | 9 | SYYDYDRFAN |
| PT1 LCDR1, Kabat | 10 | RSSESLLHSNGNTYLY |
| PT1 LCDR2, Kabat | 11 | RMSNLAS |
| PT1 LCDR3, Kabat | 12 | MQYLEYPLT |
| PT3 HCDR1, Kabat | 13 | SYAMS |
| PT3 HCDR2, Kabat | 14 | SISKGGNTYYPNSVKG |
| PT3 HCDR3, Kabat | 15 | GWGDYGWFAY |
| PT3 LCDR1, Kabat | 16 | KASQDINRYLN |
| PT3 LCDR2, Kabat | 17 | RANRLLD |

TABLE 1-continued

| Sequence name | SEQ ID NO: | Sequence |
|---|---|---|
| PT3 LCDR3, Kabat | 18 | LQYDEFPLT |
| PT1 HCDR1, Chothia | 19 | GYTFSSS |
| PT1 HCDR2, Chothia | 20 | LPGSGG |
| PT1 HCDR3, Chothia | 21 | SYYDYDRFA |
| PT1 LCDR1, Chothia | 22 | SESLLHSNGNTY |
| PT1 LCDR2, Chothia | 23 | RMS |
| PT1 LCDR3, Chothia | 24 | YLEYPL |
| PT3 HCDR1, Chothia | 25 | GFTFSSY |
| PT3 HCDR2, Chothia | 26 | SKGGN |
| PT3 HCDR3, Chothia | 27 | GWGDYGWFA |
| PT3 LCDR1, Chothia | 28 | SQDINRY |
| PT3 LCDR2, Chothia | 29 | RAN |
| PT3 LCDR3, Chothia | 30 | YDEFPL |
| PT1 VH | 35 | QVQLQQSGTELMKPGASVKISCKATGYTFSSSWMGWVKQRPGHGLEWIGDILPGSGGTNYNERFKGKASFTAETSSNTAYMQLSSLTSEDSAVYYCVRSYYDYDRFANWGQGTLVTVSA |
| PT1 VL | 36 | DIVMTQAAPSVPVTPGESVSISCRSSESLLHSNGNTYLYWFLQRPGQSPQLLIYRMSNLASGVPDRFSGSGSGTAFTLRISRVEAEDVGVYYCMQYLEYPLTFGAGTKLELK |
| PT3 VH | 37 | EVKLVESGGDLVKPGGSLKLSCAASGFTFSSYAMSWVRQNPEKRLEWVASISKGGNTYYPNSVKGRFTISRDNARNILYLQMSSLRSEDTALYYCARGWGDYGWFAYWGQVTLVTVSA |
| PT3 VL | 38 | DIKMTQSPSSMYASLGERVTITCKASQDINRYLNWFQQKPGKSPKTLIYRANRLLDGVPSRFSGSGSGQDYSLTISSLDYEDMGIYYCLQYDEFPLTFGDGTKLELK |

Although the embodiments illustrated in the Examples comprise pairs of variable regions, one from a heavy and one from a light chain, a skilled artisan will recognize that alternative embodiments may comprise single heavy or light chain variable regions. The single variable region can be used to screen for variable domains capable of forming a two-domain specific antigen-binding fragment capable of, for example, binding to PHF-tau. The screening may be accomplished by phage display screening methods using for example hierarchical dual combinatorial approach disclosed in PCT Publ. No. WO92/01047. In this approach, an individual colony containing either a H or L chain clone is used to infect a complete library of clones encoding the other chain (L or H), and the resulting two-chain specific antigen-binding domain is selected in accordance with phage display techniques as described.

Another embodiment of the invention is an isolated antibody that binds PHF-tau comprising an antigen-binding site of a heavy chain variable region (VH) of SEQ ID NO:35 and an antigen-binding site of a light chain variable region (VL) of SEQ ID NO: 36.

Another embodiment of the invention is an isolated antibody that binds PHF-tau comprising an antigen-binding site of a heavy chain variable region (VH) of SEQ ID NO:37 and an antigen-binding site of a light chain variable region (VL) of SEQ ID NO: 38.

Another embodiment of the invention is an isolated antibody that binds PHF-tau comprising heavy chain complementarity determining regions (CDRs) 1 (HCDR1), 2 (HCDR2) and 3 (HCDR3) of SEQ ID NOs:7, 8 and 9, respectively, and light chain CDRs 1 (LCDR1), 2 (LCDR2) and 3 (LCDR3) of SEQ ID NOs:10, 11 and 12, respectively.

Another embodiment of the invention is an isolated antibody that binds PHF-tau comprising heavy chain complementarity determining regions (CDRs) 1 (HCDR1), 2 (HCDR2) and 3 (HCDR3) of SEQ ID NOs:13, 14 and 15, respectively, and light chain CDRs 1 (LCDR1), 2 (LCDR2) and 3 (LCDR3) of SEQ ID NOs:16, 17 and 18, respectively.

In any of the preceding embodiments, the isolated antibody that binds PHF-tau may be humanized.

Antibodies of the present invention can be produced by a variety of techniques, for example by the hybridoma method (Kohler and Milstein *Nature* 256:495-7, 1975). Chimeric mAbs containing a light chain and heavy chain variable region derived from a donor antibody (typically murine) in association with light and heavy chain constant regions derived from an acceptor antibody (typically another mammalian species such as human) can be prepared by the method disclosed in U.S. Pat. No. 4,816,567. CDR-grafted mAbs having CDRs derived from a non-human donor immunoglobulin (typically murine) and the remaining immunoglobulin-derived parts of the molecule being derived from one or more human immunoglobulins can be prepared by techniques known to those skilled in the art such as that disclosed in U.S. Pat. No. 5,225,539. Fully human mAbs lacking any non-human sequences can be prepared from human immunoglobulin transgenic mice by techniques referenced in (Lonberg, et al. *Nature* 368:856-9, 1994, Fishwild, et al. *Nat Biotechnol* 14:845-51, 1996, Mendez, et al. *Nat Genet* 15:146-56, 1997). Human mAbs can also be prepared and optimized from phage display libraries (Knappik, et al. *J Mol Biol* 296:57-86, 2000, Krebs, et al. *J Immunol Methods* 254:67-84, 2001, Shi, et al. *J Mol Biol* 397:385-96, 2010).

Antibody humanization can be accomplished using well known methods, such as specificity determining residues resurfacing (SDRR) (U.S. Publ. No. 2010/0261620), resurfacing (Padlan et al. *Mol. Immunol.* 28:489-98, 1991), super humanization (Int. Pat. Publ. No. WO04/006955) and human string content optimization (U.S. Pat. No. 7,657, 380). Human framework sequences useful for grafting/humanization can be selected from relevant databases by those skilled in the art. The selected frameworks may further be modified to preserve or enhance binding affinity by techniques such as those disclosed in Queen et al. (Queen, et al. *Proc Natl Acad Sci USA* 86:10029-33, 1989) or in U.S. Publ. No. 2011/0092372.

Preparation of PHF-tau to be used as an antigen for immunization or isolating antibodies from phage display libraries can be done using any suitable technique. In an exemplary method, PHF-tau is isolated from brains of patients having AD using well know protocols, such as described in Greenberg and Davies (Greenberg and Davies *Proc Natl Acad Sci USA* 87:5827-31, 1990). PHF-tau may be isolated from the postmortem cortex of an Alzheimer patient. The isolated PHF-tau is characterized for its purity and hyperphosphorylation status with antibodies known to react with PHF-tau. In a typical PHF-tau preparation, the hyperphosphorylated bands migrating at about 60, 64, 68 and 72 kDa in western blot (Spillantini and Goedert *Trends Neurosci* 21:428-33, 1998) are detected by an AT8 antibody that specifically binds hyperphosphorylated PHF-tau but not dephoshporylated PHF-tau.

Antibodies of the present invention may have the characteristics of not binding control tau of SEQ ID NO:6. Such antibodies may be generated using methods described above and testing the antibodies for their lack of binding to control tau in western blots followed by Coomassie stain as described above. Control tau may be recombinantly expressed and purified using standard methods. Exemplary antibodies binding PHF-tau but not control tau are antibodies PT1 and PT3. The antibodies of the invention may further be evaluated for their specificity for example using immunohistochemistry on control and AD brain slices.

The antibodies of the invention may have affinities towards PHF-tau with a dissociation constant ($K_D$) less than or equal to about $10^{-7}$, $10^{-8}$, $10^{-9}$, $10^{-10}$, $10^{-11}$ or $10^{-12}$ M. The affinity of a given molecule for PHF-tau can be determined experimentally using any suitable method. Such methods may utilize Biacore, ProteOn or KinExA instrumentation, ELISA or competitive binding assays known to those skilled in the art.

Another aspect of the invention is an isolated antibody or fragment that competes for PHF-tau binding with a monoclonal antibody comprising an antigen-binding site of a heavy chain variable region (VH) of SEQ ID NO:35 and an antigen-binding site of a light chain variable region (VL) of SEQ ID NO:36, or an antigen-binding site of a heavy chain variable region (VH) of SEQ ID NO:37 and an antigen-binding site of a light chain variable region (VL) of SEQ ID NO:38.

Competition between binding to PHF-tau can be assayed in vitro using well known methods. For example, binding of MSD Sulfo-Tag™ NHS-ester-labeled antibody to PHF-tau in the presence of an unlabeled antibody can be assessed using immunoassay followed by electrochemiluminescence detection.

Several well known methodologies in addition to competitive binding can be employed to determine the binding epitope of the antibodies of the invention. For example, when the structures of both individual components are known, in silico protein-protein docking can be carried out to identify compatible sites of interaction. Hydrogen-deuterium (H/D) exchange can be carried out with the antigen and antibody complex to map regions on the antigen that may be bound by the antibody. Segment and point mutagenesis of the antigen can be used to locate amino acids important for antibody binding. Co-crystal structure of antibody-antigen complex is used to identify residues contributing to the epitope and paratope.

Antibodies of the invention may be monoclonal antibodies of the IgG, IgD, IgA or IgM isotypes. Antibodies of the invention may be bispecific or multispecific. An exemplary bispecific antibody may bind two distinct epitopes on PHF-tau or may bind PHF-tau and amyloid beta (Aβ). Another exemplary bispecific antibody may bind PHF-tau and an endogenous blood-brain barrier transcytosis receptor such as insulin receptor, transferring receptor, insulin-like growth factor-1 receptor, and lipoprotein receptor. An exemplary antibody is of IgG1 type.

Immune effector properties of the antibodies of the invention may be enhanced or silenced through Fc modifications by techniques known to those skilled in the art. For example, Fc effector functions such as C1q binding, complement dependent cytotoxicity (CDC), antibody-dependent cell-mediated cytotoxicity (ADCC), phagocytosis, down regulation of cell surface receptors (e.g., B cell receptor; BCR), etc. can be provided and/or controlled by modifying residues in the Fc responsible for these activities. Pharmacokinetic properties could also be enhanced by mutating residues in the Fc domain that extend antibody half-life (Strohl *Curr Opin Biotechnol* 20:685-91, 2009).

Additionally, antibodies of the invention can be post-translationally modified by processes such as glycosylation, isomerization, deglycosylation or non-naturally occurring covalent modification such as the addition of polyethylene glycol moieties (pegylation) and lipidation. Such modifications may occur in vivo or in vitro. For example, the antibodies of the invention can be conjugated to polyethylene glycol (PEGylated) to improve their pharmacokinetic profiles. Conjugation can be carried out by techniques known to those skilled in the art. Conjugation of therapeutic antibodies with PEG has been shown to enhance pharmacodynamics while not interfering with function (Knight et al. *Platelets* 15:409-18, 2004, Leong, et al. *Cytokine* 16:106-19, 2001, Yang, et al. *Protein Eng* 16:761-70, 2003).

Another embodiment of the invention is an isolated polynucleotide encoding the antibodies of the invention or their complement, or fragments thereof. Exemplary isolated polynucleotides are polynucleotides encoding polypeptides comprising an immunoglobulin heavy chain CDRs HCDR1, HCDR2 and HCDR3 shown in SEQ ID NOs:7, 8 and 9 or 13, 14 and 15, respectively, or polypeptides comprising an immunoglobulin light chain CDRs LCDR1, LCDR2 and LCDR3 shown in SEQ ID NOs:10, 11 and 12 or 16, 17 and 18, respectively, and polynucleotides having a sequence shown in SEQ ID NOs:31-34, encoding antibody variable regions of the invention. Other polynucleotides which, given the degeneracy of the genetic code or codon preferences in a given expression system, encode the antibodies of the invention are also within the scope of the invention. The isolated nucleic acids of the present invention can be made using well known recombinant or synthetic techniques. DNA encoding the monoclonal antibodies is readily isolated and sequenced using methods known in the art. Where a hybridoma is produced, such cells can serve as a source of such DNA. Alternatively, using display techniques wherein the coding sequence and the translation product are linked, such as phage or ribosomal display libraries, the selection of the binder and the nucleic acid is simplified. After phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria.

Another embodiment of the invention is a vector comprising at least one polynucleotide of the invention. Such vectors may be plasmid vectors, viral vectors, transposon based vectors or any other vector suitable for introduction of the polynucleotides of the invention into a given organism or genetic background by any means.

Another embodiment of the invention is a host cell comprising any of the polynucleotides of the invention. Such host cells may be eukaryotic cells, bacterial cells, plant cells or archeal cells. Exemplary eukaryotic cells may be of mammalian, insect, avian or other animal origins Mammalian eukaryotic cells include immortalized cell lines such as hybridomas or myeloma cell lines such as SP2/0 (American Type Culture Collection (ATCC), Manassas, Va., CRL-1581), NS0 (European Collection of Cell Cultures (ECACC), Salisbury, Wiltshire, UK, ECACC No. 85110503), FO (ATCC CRL-1646) and Ag653 (ATCC CRL-1580) murine cell lines. An exemplary human myeloma cell line is U266 (ATTC CRL-TIB-196). Other useful cell lines include those derived from Chinese Hamster Ovary (CHO) cells such as CHO-K1SV (Lonza Biologics), CHO-K1 (ATCC CRL-61, Invitrogen) or DG44.

Another embodiment of the invention is a method of making an antibody that binds PHF-tau comprising culturing a host cell of the invention and recovering the antibody produced by the host cell. Methods of making antibodies and purifying them are well known in the art.

Methods of Treatment

Anti-PHF-tau antibodies of the invention or fragments thereof, including Fab, (Fab')2, scFv fragments, or antibodies comprising antigen-binding sites of the antibodies of the invention can be used to treat, reduce or prevent symptoms in patients having a neurodegenerative disease that involves pathological aggregation of tau within the brain, such as patients suffering from AD or any other tauopathy. While not wishing to be bound by any particular theory, the antibodies of the invention may exert their beneficial effect by reducing pathological tau aggregation and hence the amount of PHF-tau in the brain. The antibodies of the invention may be used to treat an animal patient belonging to any classification. Examples of such animals include mammals such as humans, rodents, dogs, cats and farm animals. For example, the antibodies of the invention are useful in the preparation of a medicament for treatment of AD wherein the medicament is prepared for administration in dosages defined herein.

Another embodiment of the invention is a method of reducing aggregation of tau in patients in need thereof comprising administering to the patient a therapeutically effective amount of the isolated antibody of the invention for a time sufficient to reduce the aggregation of tau.

Another embodiment of the invention is a method of treating or reducing symptoms of a neurodegenerative disease that involves aggregation of tau in a patient comprising administering to the patient a therapeutically effective amount of the isolated antibody of the invention for a time sufficient to treat or reduce symptoms of the neurodegenerative disease.

In any of the embodiments above, the neurodegenerative disease that involves aggregation of tau is a tauopathy.

In any of the embodiments above, the isolated antibody comprises an antibody that binds PHF-tau comprising an antigen-binding site of a VH of SEQ ID NO:35 and an antigen-binding site of a VL of SEQ ID NO:36.

In any of the embodiments above, the isolated antibody comprises an antibody that binds PHF-tau comprising an antigen-binding site of a VH of SEQ ID NO:37 and an antigen-binding site of a VL of SEQ ID NO: 38.

As used herein a "tauopathy" encompasses any neurodegenerative disease that involves the pathological aggregation of tau within the brain. In addition to familial and sporadic AD, other exemplary tauopathies are frontotemporal dementia with parkinsonism linked to chromosome 17 (FTDP-17), progressive supranuclear palsy, corticobasal degeneration, Pick's disease, progressive subcortical gliosis, tangle only dementia, diffuse neurofibrillary tangles with calcification, argyrophilic grain dementia, amyotrophic lateral sclerosis parkinsonism-dementia complex, Down syndrome, Gerstmann-Sträussler-Scheinker disease, Hallervorden-Spatz disease, inclusion body myositis, Creutzfeld-Jakob disease, multiple system atropy, Niemann-Pick disease type C, prion protein cerebral amyloid angiopathy, subacute sclerosing panencephalitis, myotonic dystrophy, non-guanamian motor neuron disease with neurofibrillary tangles, postencephalitic parkinsonism, and chronic traumatic encephalopathy, such as dementia pugulistica (boxing disease). (Morris, et al. *Neuron* 70:410-26, 2011).

A tauopathy-related behavioral phenotype includes cognitive impairments, early personality change and disinhibition, apathy, abulia, mutism, apraxia, perseveration, stereotyped movements/behaviors, hyperorality, disorganization, inability to plan or organize sequential tasks, selfishness/callousness, antisocial traits, a lack of empathy, halting, agrammatic speech with frequent paraphasic errors but relatively preserved comprehension, impaired comprehension and word-finding deficits, slowly progressive gait instability, retropulsions, freezing, frequent falls, non-levodopa responsive axial rigidity, supranuclear gaze palsy, square wave jerks, slow vertical saccades, pseudobulbar palsy, limb apraxia, dystonia, cortical sensory loss, and tremor.

Patients amenable to treatment include asymptomatic individuals at risk of AD or other tauopathy, as well as patients presently showing symptoms. Patients amenable to treatment include individuals who have a known genetic risk of AD, such as a family history of AD or presence of genetic risk factors in the genome. Exemplary risk factors are mutations in the amyloid precursor protein (APP), especially at position 717 and positions 670 and 671 (Hardy and Swedish mutations, respectively). Other risk factors are mutations in the presenilin genes, PS1 and PS2, and ApoE4, family history of hypercholesterolemia or atherosclerosis. Individuals presently suffering from AD can be recognized from characteristic dementia by the presence of risk factors described above. In addition, a number of diagnostic tests are available to identify individuals who have AD. These include measurement of cerebrospinal fluid tau and A1342 levels. Elevated tau and decreased Aβ42 levels signify the presence of AD. Individuals suffering from AD can also be diagnosed by AD and Related Disorders Association criteria.

Administration/Pharmaceutical Compositions

Anti-PHF-tau antibodies of the invention are suitable both as therapeutic and prophylactic agents for treating or preventing neurodegenerative diseases that involves pathological aggregation of tau, such as AD or other tauopathies. In asymptomatic patients, treatment can begin at any age (e.g., at about 10, 15, 20, 25, 30 years). Usually, however, it is not necessary to begin treatment until a patient reaches about 40, 50, 60, or 70 years. Treatment typically entails multiple dosages over a period of time. Treatment can be monitored by assaying antibody, or activated T-cell or B-cell responses to the therapeutic agent over time. If the response falls, a booster dosage is indicated.

In prophylactic applications, pharmaceutical compositions or medicaments are administered to a patient susceptible to, or otherwise at risk of, AD in an amount sufficient to eliminate or reduce the risk, lessen the severity, or delay the outset of the disease, including biochemical, histologic and/or behavioral symptoms of the disease, its complications and intermediate pathological phenotypes presented during development of the disease. In therapeutic applications, compositions or medicaments are administered to a patient suspected of, or already suffering from, such a disease in an amount sufficient to reduce, arrest, or delay any of the symptoms of the disease (biochemical, histologic and/or behavioral). Administration of a therapeutic may reduce or eliminate mild cognitive impairment in patients that have not yet developed characteristic Alzheimer's pathology. An amount adequate to accomplish therapeutic or prophylactic treatment is defined as a therapeutically- or prophylactically-effective dose. In both prophylactic and therapeutic regimes, compositions or medicaments are usually administered in several dosages until a sufficient immune response has been achieved.

Anti-PHF-tau antibodies or fragments thereof of the invention may be administered in combination with other agents that are effective for treatment of related neurodegenerative diseases. In the case of AD, antibodies of the invention may be administered in combination with agents that reduce or prevent the deposition of amyloid-beta (Aβ). It is possible that PHF-tau and Aβ pathologies are synergistic. Therefore, combination therapy targeting the clearance of both PHF-tau and Aβ and Aβ-related pathologies at the same time may be more effective than targeting each individually.

In the case of Parkinson's Disease and related neurodegenerative diseases, immune modulation to clear aggregated forms of the α-synuclein protein is also an emerging therapy. A combination therapy which targets the clearance of both tau and α-synuclein proteins simultaneously may be more effective than targeting either protein individually.

In the methods of the invention, the "therapeutically effective amount" of the antibody in the treatment or ameliorating symptoms of a tauopathy can be determined by standard research techniques. For example, the dosage of the antibody can be determined by administering the agent to relevant animal models well known in the art.

In addition, in vitro assays can optionally be employed to help identify optimal dosage ranges. Selection of a particular effective dose can be determined (e.g., via clinical trials) by those skilled in the art based upon the consideration of several factors. Such factors include the disease to be treated or prevented, the symptoms involved, the patient's body mass, the patient's immune status and other factors known by the skilled artisan. The precise dose to be employed in the formulation will also depend on the route of administration, and the severity of disease, and should be decided according to the judgment of the practitioner and each patient's circumstances. Effective doses can be extrapolated from dose-response curves derived from in vitro or animal model test systems.

The mode of administration for therapeutic use of the antibodies of the invention may be any suitable route that delivers the agent to the host. Pharmaceutical compositions of these antibodies are useful for parenteral administration, e.g., intradermal, intramuscular, intraperitoneal, intravenous, subcutaneous, intranasal or intracranial or they can be administered into the cerebrospinal fluid of the brain or spine.

The antibodies of the invention may be prepared as pharmaceutical compositions containing an effective amount of the antibody as an active ingredient in a pharmaceutically acceptable carrier. The term "carrier" refers to a diluent, adjuvant, excipient, or vehicle with which the antibody is administered. Such pharmaceutical vehicles can be liquids, such as water and oils, including those of petroleum, animal, vegetable or synthetic origin, such as peanut oil, soybean oil, mineral oil, sesame oil and the like. For example, 0.4% saline and 0.3% glycine can be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the antibodies of the invention in such pharmaceutical formulation can vary widely, i.e., from less than about 0.5%, usually at or at least about 1% to as much as 15 or 20% by weight and will be selected primarily based on required dose, fluid volumes, viscosities, etc., according to the particular mode of administration selected.

The treatment may be given in a single dose schedule, or as a multiple dose schedule in which a primary course of treatment may be with 1-10 separate doses, followed by other doses given at subsequent time intervals required to maintain and or reinforce the response, for example, at 1-4 months for a second dose, and if needed, a subsequent dose(s) after several months. Examples of suitable treatment schedules include: (i) 0, 1 month and 6 months, (ii) 0, 7 days and 1 month, (iii) 0 and 1 month, (iv) 0 and 6 months, or other schedules sufficient to elicit the desired responses expected to reduce disease symptoms, or reduce severity of disease.

Thus, a pharmaceutical composition of the invention for intramuscular injection could be prepared to contain 1 ml sterile buffered water, and between about 1 ng to about 100 mg, about 50 ng to about 30 mg or about 5 mg to about 25 mg of an antibody of the invention. Similarly, a pharmaceutical composition of the invention for intravenous infusion could be made up to contain about 250 ml of sterile Ringer's solution, and about 1 mg to about 30 mg or about 5 mg to about 25 mg of an antibody of the invention. Actual methods for preparing parenterally administrable compositions are well known and are described in more detail in, for example, "Remington's Pharmaceutical Science", 15th ed., Mack Publishing Company, Easton, Pa.

The antibodies of the invention can be lyophilized for storage and reconstituted in a suitable carrier prior to use. This technique has been shown to be effective with antibody and other protein preparations and art-known lyophilization and reconstitution techniques can be employed.

Diagnostic Methods and Kits

Antibodies of the invention may be used in methods of diagnosing AD or other tauopathy in a subject. This method involves detecting, in the subject, the presence of PHF-tau using a diagnostic reagent such as an antibody or a fragment thereof of the present invention.

PHF-tau may be detected in a biological sample from a subject (e.g., blood, urine, cerebral spinal fluid) by contacting the biological sample with the diagnostic antibody reagent, and detecting binding of the diagnostic antibody reagent to PHF-tau in the sample from the subject. Assays for carrying out the detection include well known methods such as ELISA, immunohistochemistry, western blot, or in vivo imaging. Exemplary diagnostic antibodies are antibodies PT1 and PT3 of the invention, and are of IgG1, κ type.

Diagnostic antibodies or similar reagents can be administered by intravenous injection into the body of the patient, or directly into the brain by any suitable route that delivers the agent to the host as exemplified above. The dosage of antibody should be within the same ranges as for treatment methods. Typically, the antibody is labeled, although in some methods, the primary antibody with affinity for PHF-tau is unlabelled and a secondary labeling agent is used to bind to the primary antibody. The choice of label depends on the means of detection. For example, a fluorescent label is suitable for optical detection. Use of paramagnetic labels is suitable for tomographic detection without surgical intervention. Radioactive labels can also be detected using PET or SPECT.

Diagnosis is performed by comparing the number, size, and/or intensity of labeled PHF-tau, tau aggregates, and/or neurofibrillary tangles in a sample from the subject or in the subject, to corresponding baseline values. The baseline values can represent the mean levels in a population of undiseased individuals. Baseline values can also represent previous levels determined in the same subject.

The diagnostic methods described above can also be used to monitor a subject's response to therapy by detecting the presence of PHF-tau in a subject before, during or after the treatment. A decrease in values relative to baseline signals a positive response to treatment. Values can also increase temporarily in biological fluids as pathological tau is being cleared from the brain.

The present invention is further directed to a kit for performing the above described diagnostic and monitoring methods. Typically, such kits contain a diagnostic reagent such as the antibodies of the invention, and optionally a detectable label. The diagnostic antibody itself may contain the detectable label (e.g., fluorescent molecule, biotin, etc.) which is directly detectable or detectable via a secondary reaction (e.g., reaction with streptavidin). Alternatively, a second reagent containing the detectable label may be utilized, where the second reagent has binding specificity for the primary antibody. In a diagnostic kit suitable for measuring PHF-tau in a biological sample, the antibodies of the kit may be supplied prebound to a solid phase, such as to the wells of a microtiter dish.

The contents of all cited references (including literature references, issued patents, published patent applications, and co-pending patent applications) cited throughout this application are hereby expressly incorporated by reference.

EXAMPLE 1

Purification of Paired Helical Filament-tau (PHF-tau)

PHF-tau was partially purified by a modified method of Greenberg and Davies (Greenberg and Davies *Proc Natl Acad Sci USA* 87:5827-31, 1990). Briefly, postmortem tissue from the cortex obtained from a histologically confirmed Alzheimer patient was partially purified. Typically, 5 mg of frontal cortex was homogenized in 10 vol of cold buffer Buffer H (10 mM Tris, 800 mM NaCl, 1 mM EGTA and 10% sucrose/pH 7.4) using a glass/Teflon Potter tissue homogenizer (IKA Works, Inc; Staufen, Germany) at 1000 rpm. The homogenized material was centrifuged at 27000 g for 20 min in a Sorvall rotor SS34. The pellet was discarded and the supernatant was adjusted to a final concentration of 1% (w/v) N-lauroylsarcosine and 1% (v/v) 2-mercaptoethanol and incubated for 2 h at 37° C. Subsequently the supernatant was centrifuged at 108000 g for 35 min at 20° C. in a Beckman 60Ti rotor. The pellet was carefully washed in PBS and suspended in PBS. The supernatant was centrifuged a second time as described and the final pellet was dissolved, aliquoted and frozen at −80° C. The quality of the PHF-tau preparations were evaluated on a 12% SDS-PAGE and western blot with anti-tau antibodies AT8 and HT7 (ThermoScientific, Rockford, Ill.). AT8 detects PHF-tau phosphorylated at S202/T205, but does not bind to non-phosphorylated PHF-tau nor to the wild type tau. HT7 binds to a non-phosphorylated epitope at Tau amino acids 159-163 (of SEQ ID NO: 6), and recognizes both tau and PHF-tau. A good quality PHF-tau preparation is composed of 4 bands having molecular weights of about 60, 64, 66 and 72 kDa on a Western blot detected with an antibody reactive with hyperphosphorylated PHF-tau such as AT8. Two separate PHF-tau preparations with comparable quality and purity were made from the same brain sample. Preparation 1 was used for immunization.

EXAMPLE 2

Generation of Monoclonal Antibodies Against PHF-tau

Anti-PHF-tau antibodies were generated using standard hybridoma technology in normal Balb/c mice (Kohler and Milstein Nature 256:495-7, 1975). Obtained hybridomas were seeded in 96-well plates and screened after 10 days in a direct ELISA on 25 ng/well coated PHF-tau as described below. Positive cells were tested for cross-reactivity on 10 ng/well coated with control tau (SEQ ID NO:6) expressed in E. Coli BL21 cells and purified by heat treatment and ammonium sulphate precipitation, and were immediately subcloned and positive clones were frozen in liquid nitrogen. All hybridomas were grown in Dulbecco's modified Eagle's medium supplemented with 10% foetal calf serum (Hyclone, Europe), Hybridoma Fusion Cloning Supplement (2%) (Roche, Brussels, Belgium) 2% HT (Sigma, USA), 1 mM sodium pyruvate, 2 mM L-glutamine and penicillin (100 U/ml) and Streptomycin (50 mg/ml).

Antibody variable regions were cloned from select hybridoma cells onto mouse IgG1/IgG2/κ background and expressed and purified using routine methods.

Direct ELISA for Antibody Selection 25 ng/well PHF-tau was coated overnight at 4° C. in NUNC Maxisorp (Life Technologies) flat-bottom high-binding 96-well micro titer plates in 50 µl/well coating buffer (10 mM Tris, 10 mM NaCl, and 10 mM NaN3, pH 8.5). The next day, the plates were blocked with 75 µl/well of 0.1% casein in PBS for 60 min at room temperature. Next, 50 µl hybridoma supernatant was added and incubated for 1 h at 37° C. After washing, the bound monoclonal antibodies were detected with 50 µl/well of Sheep-anti-mouse IgG conjugated with horseradish peroxidase for 1 hr at 37° C. (Amersham-Pharmacia Biotech). Both reagents were diluted in 0.1% Casein/PBS. The plates were washed and 50 µl of a solution of 0.42 mM 3,5,3',5'-tetramethyl-benzidine, 0.003% (v/v) $H_2O_2$ in 100 mM citric acid and 100 mM disodium hydrogen phosphate (pH 4.3) was added as the substrate. The reaction was allowed to proceed for maximum 15 min on a plate shaker at room temperature, after which the color development was stopped with 2 N $H_2SO_4$, 50 µl/well and the plates, were read on a micro titer plate reader at 450 nm (Thermomax, Molecular Devices).

Specificity of the Monoclonal Antibodies

Select antibodies obtained from the hybridoma screen were tested for their cross-reactivity with recombinantly expressed control tau (SEQ ID NO:6). 500 ng of PHF-tau and 200 ng of control tau were loaded on a NuPAGE® Novex® Bis-Tris 4-12% gel and blotted on a nitrocellulose membrane by use of an iBlot system (Invitrogen), according to the manufacturer's instructions. Membranes were blocked for 1 hour with Tris-Buffered Saline Tween-20 (TBS-T; 1M Tris, 150 mM NaCl and 0.05% Tween-20, pH 8.5) containing non fat dry milk (NFDM) (5% w/v; Biorad) and washed three times in TBS-T. Incubation with the primary control antibodies (1 µg/ml) HT7, AT8, AT100 (ThermoScientific, Rockford, Ill.), and BT2 diluted in TBS-T containing NFDM (5% w/v) was overnight at 4° C. PT1, PT2, PT3, PT4 and PT5 monoclonal antibodies selected from the hybridoma screen were added in culture supernatant containing 10% FCS. Primary antibodies were detected using Sheep-anti-mouse Ig conjugated with HRPO (1:20000 in TBS-T, Amersham Biosciences) via West Dura® enhanced chemiluminescence (Pierce, Thermoscientific). Signals were captured by the Lumi-imaging system (Roche Diagnostic). PT1 and PT3 reacted with PHF-tau and did not react with control tau in western blots. PT2 was reactive with both proteins. Binding profiles of HT7 and AT8 are described above. AT100 binds to phosphorylated Ser212/Thr214 and binds to PHF-tau but not wild type tau. BT2 recognizes a non-phosphorylated epitope comprising S199/S202, and thus recognizes wild type tau but not PHF-tau.

Competitive Epitope Binding

Monoclonal antibodies PT1, PT2, PT3, PT4, PT5, AT8 (ThermoScientific, Rockford, Ill.), AT100 (ThermoScientific, Rockford, Ill.) and HT7 (MN1000) (Thermo Scientific, Rockford, Ill.) were evaluated for competitive binding to PHF-tau or phosphorylated tau peptides. Antibodies were labeled using MSD® SULFO-TAG NHS Ester (Meso Scale Discovery) according to the manufacturer's instruction For competition with labeled PT1, PT3, AT100 and HT7, 5 µL (50 µg/mL)/well of enriched PHF-Tau proteins (purified as described above) was coated on MSD HighBind plate (Meso Scale Discovery, Gaithersburg, Md.) for 2 hr at room temperature (RT). For competition with AT8, 25 µL of 0.1 mg/well synthetic biotinylated and pegylated peptide RSGYSSPG(pS)PG(pT)PGSRSR-OH (New England Peptide, LLC., Gardner, Mass.) (SEQ ID NO:39) corresponding to residues 194-211 of control tau (SEQ ID NO:6) phosphorylated at residues corresponding to S202/T205 in control tau was coated on Streptavidin-charged plates (Meso Scale Discovery, Gaithersburg, Md.). After coating, wells were blocked with 150 µL of 5% MSD Blocker A buffer at RT for 2 hr, and washed three times with 0.1 M HEPES buffer, pH 7.4. 25 µL of a mixture of labeled individual anti-tau antibody (10 nM or 50 nM) and serial dilutions of various unlabeled competitor antibodies (1 nM to 2 µM) was added on each well. The plates were incubated for 2 hours at RT with gentle shaking and washed 3 times as above. 150 µL/well of diluted MSD Read Buffer T was added and the plates were read in a SECTOR Imager 6000 (Meso Scale Discovery, Gaithersburg, Md.).

Non-overlapping epitopes of anti-Tau mAbs HT7, AT100 and AT8 are described above. Based on the published data, these antibodies were not expected to compete with each other in binding to Tau proteins or peptides.

Based on competition assays performed, none of the antibodies competed with each other for binding, indicating that they all bind to different epitopes. In each experiment, only self-inhibition was observed. FIGS. 1-5 show results of competition assays with labeled AT8, PT1, PT3, AT100, and HT7, respectively.

EXAMPLE 3

Anti-PHF Tau Antibodies Reduce PHF-tau Accumulation in vivo 5-month old female P301L mice (Taconic, cat#002508) were treated once weekly with mouse IgG1, saline, PT3 (500 µg/mouse) or AT8 (expressed from hybridoma ECACC, deposit number 9110086) for 5 months. Mice were anesthetized, perfused with cold PBS and the brains dissected on ice. For each mouse, one brain hemisphere was homogenized in 10 volume of H-buffer, followed by centrifugation at 21,000 g for 20 min at 4° C. The resulting supernatant was further centrifuged at 100,000 g for 60 min. After centrifugation, the pellet (fraction P1) was recovered and re-suspended with lysis buffer for Western and ELISA analyses, as described by Chai et al. J Biol Chem 286:34457-67, 2011. For cortex samples, the fraction P1 was further treated with 1% (w/v) N-lauroylsarcosine and ultracentrifuged to further enrich PHF-tau in the pellet. Male P301L mice were found to have low transgene expression and were not included in the analyses.

Figure 6A:
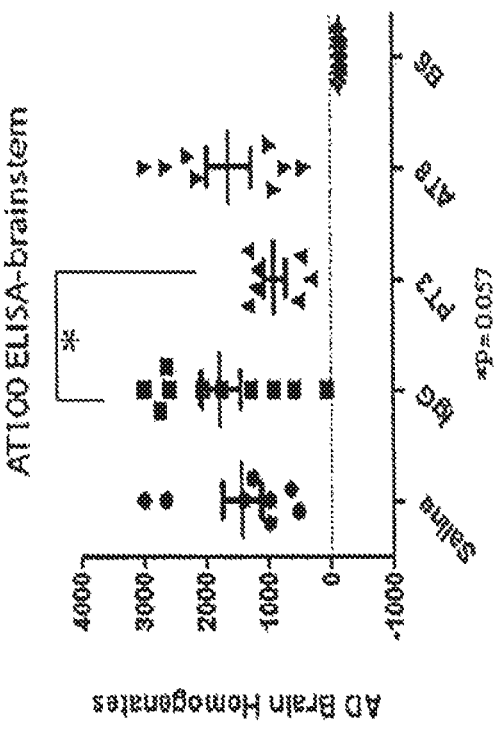
FIGS. 6A-6C show an analysis of phosphorylated tau in brainstem homogenates (fraction P1) of 5 month old female P301L transgenic animals treated with saline, mouse IgG1, PT3 or AT8 as indicated in the figure, or from non-treated non-transgenic animals (B6). ELISA was done using AT8 (A) or AT100 (B) as capture antibodies followed by biotinylated-HT7 and avidin-HRP. ELISA signals are plotted as a relative amount of AD brain homogenate (ng/ml) providing the same ELISA signal as an average samples from a non-transgenic animal (B6). Data are plotted individually together with mean+/−S.D. p values for differences between PT3- and IgG1-treated animals are indicated. (C) Western blot of brainstem homogenates fraction P1 from IgG1- or PT3-treated animals using AT100. Signal from homogenates of 10 animals treated with IgG1 (IgG1-1 to IgG1-10) and 7 animals treated with PT3 (PT3-1, PT3-2, PT3-7 to PT3-10) are shown. Actin was used as a loading control.

Phosphorylated tau was measured in brainstem homogenates (fraction P1) with sandwich ELISA using antibodies AT8 and AT100 as capture antibodies followed by detection by biotinylated HT7 and avidin-HRP (FIGS. 6A and 6B), and with AT100 in a western blot (FIG. 6C) essentially as described in Chai et al. *J Biol Chem* 286:34457-67, 2011. Briefly, the P1 pellet was resuspended with lysis buffer (Cell Signaling) P1 pellet samples were incubated in AT8 or AT100 (Thermo Scientific) pre-coated wells and the biotin labeled HT-7 antibody. Samples were then washed 5 times with buffer, followed by incubation with avidin-HRP for one hour. Following this, samples were incubated with one step TMB substrate (Thermo Scientific) for 30 min, followed by 2N $H_2SO_4$. Finally, the reaction was read at 450 nm and the quantity of AT8- or AT100-reactive tau in brain was determined using a standard curve derived from human AD brain homogenates, and plotted as a relative amount of AD brain homogenate (ng/ml) providing the same ELISA signal as an average samples from a non-transgenic animal (B6).

A statistically significant decrease or trend towards significance in phosphorylated tau was seen in P301L transgenic animals treated with PT3 when compared to the isotype control administered animals in ELISA assays using either AT100 (p=0.057) or AT8 (p=0.0475) to detected phosphorylation (ELISA signal: Saline group (1135±228.8); IgG1 group (1344±245.6); PT3 group (660.5±134.5); AT8 group (1271±274)).

Figure 6B:
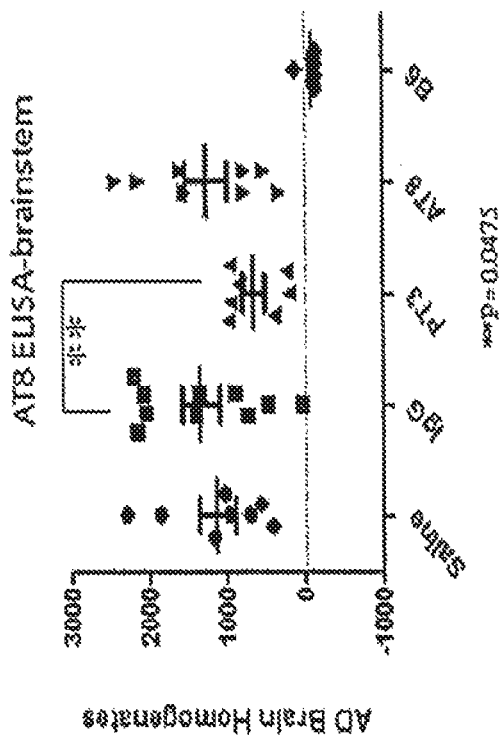
Figure 6C:
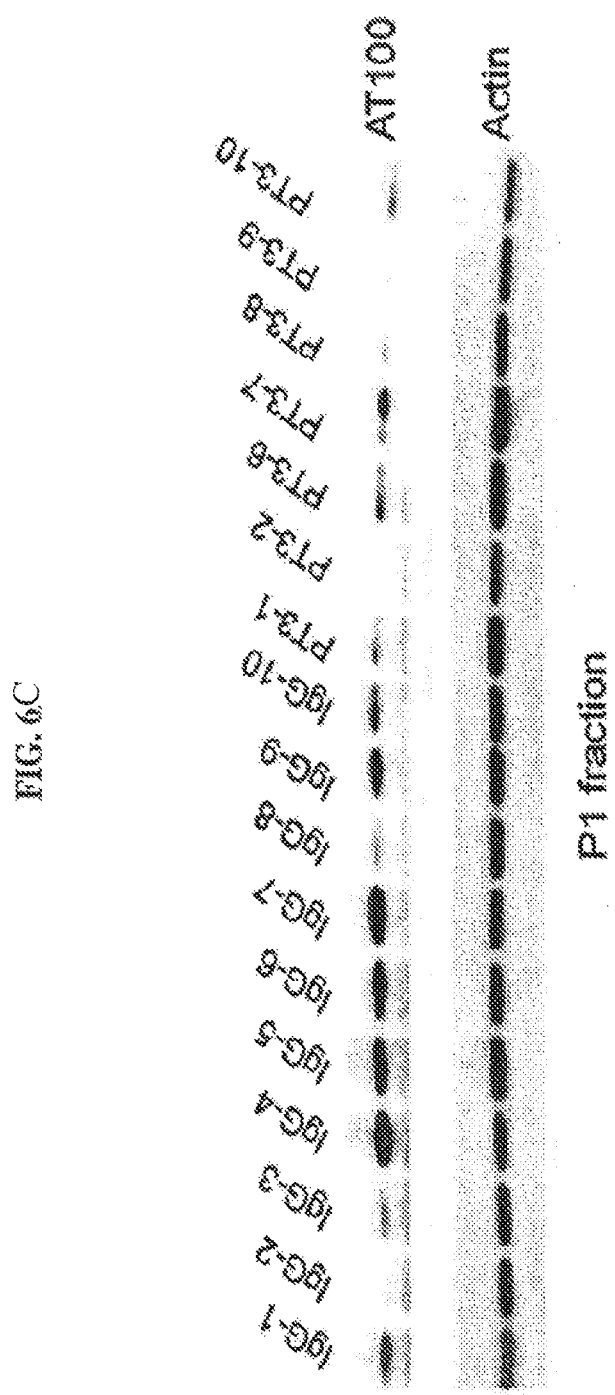
Figure 7A:
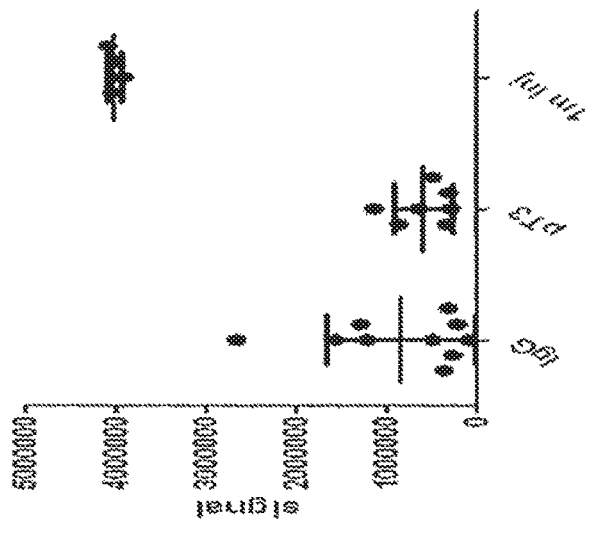
FIGS. 7A-7C show the levels of total tau in (A) sarcosyl soluble (pT4 soluble), (B) total tau in insoluble (pT4 insoluble) and (C) phosphorylated tau in insoluble (AT8 insoluble) cortex homogenates derived from 5-month old female P301L transgenic mice treated with PT3 or isotype control (IgG) as indicated in the figure. Levels are shown as a measure of a signal from ELISA plotted individually together with mean+/−SD. The sample 1 m inj is a positive control sample derived from a P301L mouse brain injected with a tau aggregate.
Figure 7B:
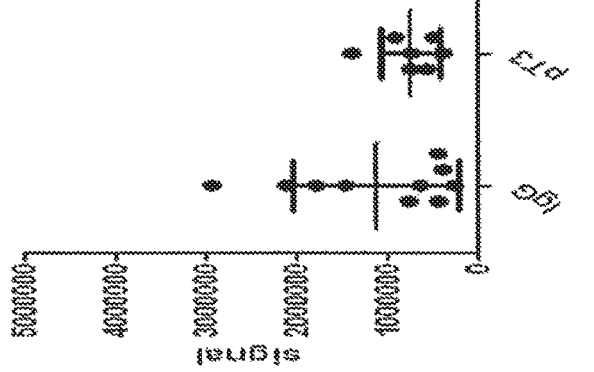
Figure 7C:
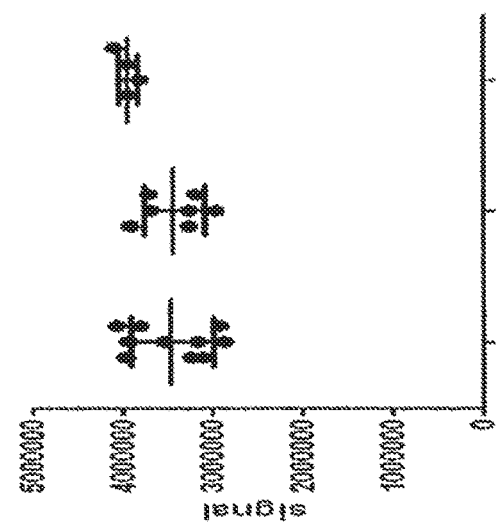

To confirm the data obtained with ELISA, brainstem homogenates (fraction P1) from IgG1- or PT3-treated animals were analyzed on western blot by detecting PHF-tau using AT100 antibody. The filters were blotted using anti-actin antibody as a loading control (FIG. 6B). Western blots showed attenuated PHF-tau amount detected with AT100 antibody when compared to the animals treated with IgG1.

For cortex analysis, both sarcosyl soluble (representing soluble tau) and insoluble (representing PHF-tau) cortex fractions were analyzed by sandwich ELISA using a pan-tau antibody (PT4) or phospho-tau antibody (AT8) for capturing followed by a biotin-pan-tau antibody (hTau10) followed by HRP-avidin Animals treated with PT3 had similar levels of total tau in comparison to animals treated with the isotype control IgG1. A trend towards lower PHF-tau levels were evident in animals treated with PT3 when compared to the isotype control in the N-lauroylsarcosine insoluble fractions (ELISA capture with PT4: IgG group: 851026±261198 and PT3 group: 585639±120498; ELISA, capture with AT8: IgG group: 1125886±286240 (N=10) and pT3 group: 746582±124970 (N=7)).

EXAMPLE 4

Characterization of Anti-PHF-tau Antibodies

Affinity Determination

The interactions of monoclonal antibodies PT1 and PT3 with recombinant human soluble tau or PHF-tau were studied by ProteOn. All interactions were studied at 25° C. using PBS pH 7.4, supplemented with 3 mM EDTA, and 0.005% Tween-20 as running or system buffer. Two different experiment formats were used, one for the interaction with recombinantly expressed control tau and another for the interaction with PHF-tau. In these experiments HT7 (Pierce, cat #MN1000), a mouse anti-tau antibody was used as a positive control.

To study the interaction with recombinantly expressed control tau a biosensor surface was prepared by coupling an anti-human or anti-mouse IgG Fcγ fragment specific antibody (Ab) to the surface of a GLC (ProteOn) sensor chip using each manufacturer's instructions for amine-coupling chemistry (~5000 response units (RU)). The coupling buffer was 10 mM sodium acetate, pH 4.5. The anti-PHF-tau antibodies were diluted in the running buffer and injected to obtain a capture of 60-130 RUs. Capture of anti-PFH-Tau mAbs was followed by injection of recombinantly expressed control tau (Tau-441, Sigma catalog# T0576-50 µg) in solution (0.1 to 75 nM in 5-fold dilutions). The association was monitored for 2 minutes (80 µL injected at 40 µL/min). The dissociation was monitored for 10 minutes. Regeneration of the sensor surface was obtained with 0.85% $H_3PO_4$, or 0.85% $H_3PO_4$ followed by 50 mM NaOH. The data were fit using a 1:1 binding model. The data were fit using a 1:1 binding model.

TABLE 2

| mAb | Antigen | $k_{on}$ ($M^{-1}s^{-1}$) | $k_{off}$ ($s^{-1}$) | *$K_D$ (pM) |
|---|---|---|---|---|
| PT1 | Control Tau | ** | | |
| PT1 | PHF-Tau | 2.01E+05 | 6.47E−05 | 322 |
| PT3 | Control Tau | *** | | |
| PT3 | PHF-Tau | (1.23 ± 0.06)E+06 | (2.18 ± 0.28)E−05 | 18 ± 2 |

*For PHF-tau this is the apparent intrinsic affinity where KD is obtained as the ratio of koff1/kon−1 derived from a fit performed using a bivalent binding model.
** No significant binding
*** No binding in 4 of 5 experiments To study the interaction with PHF-tau a biosensor surface was prepared by capture-coupling PHF-tau using HT7 as the capture reagent. Additional preparation of the PHF-tau as described earlier was required for ProteOn to limit the amount of insoluble material entering the fluidics. PHF-tau as described above was additionally prepared by 2-times centrifugation at 5000 g, 5° C., 10 min where the supernatant from the second centrifugation was then diluted 1/20 or 1/40 in running buffer. To prepare the chip, HT7 was covalently immobilized to the surface of a GLC (ProteOn) sensor chip using each manufacturer's instructions for amine-coupling chemistry (~3000 response units (RU)). The coupling buffer was 10 mM sodium acetate, pH 4.5. After HT7 immobilization PHF-tau was injected and captured (~300 RU) by HT7. After capture, PHF-tau was covalently immobilized to the sensor chip by activation of the chip using each manufacturer's instructions for amine-coupling chemistry. Remaining reactive sites were finally blocked by injection of ethanolamine After preparation and stabilization of the PHF-tau-modified surface and reference surface (containing no antigen), the anti-PHF-tau antibodies were diluted in the running buffer and injected in solution (0.1-75 nM in 5-fold dilutions). The association was monitored for 3 minutes (120 µL injected at 40 µL/min). The dissociation was monitored for 10 or 15 minutes. Regeneration of the sensor surface was obtained with 10 mM Gly pH 2. The data were fit using a bivalent binding model where the apparent intrinsic affinity was reported as the ratio of koff-1/kon-1.

Based on the ProteOn experiments PT1 bound PHF-tau with 322 pM affinity and showed no binding to control tau under the conditions tested (Table 2). PT3 bound PHF-tau with 18±2 pM affinity and showed no binding to control tau in 4 out of 5 measurements under the conditions tested. One out of the 5 ProteOn measurements showed weak binding which could be used to estimate affinity >75 nM on the basis of the highest concentration of control tau used.

The present invention now being fully described, it will be apparent to one of ordinary skill in the art that many changes and modifications can be made thereto without departing from the spirit or scope of the appended claims.

We claim:

1. An isolated antibody that binds paired helical filament tau (PHF-tau) comprising a heavy chain complementarity determining region (HCDR) 1, a heavy chain complementarity determining region (HCDR) 2 and a heavy chain complementarity determining region (HCDR) 3 of a heavy chain variable region (VH) of SEQ ID NO: 35, and a light chain complementarity determining region (LCDR) 1, a light chain complementarity determining region (LCDR) 2 and a light chain complementarity determining region (LCDR) 3 of a light chain variable region (VL) of SEQ ID NO: 36.

2. A pharmaceutical composition comprising the antibody of claim 1 and a pharmaceutically acceptable carrier.

3. The isolated antibody of claim 1, wherein the antibody is humanized.

4. A vector comprising a polynucleotide encoding an antibody of claim 1.

5. A host cell comprising the vector of claim 4.

6. The isolated antibody of claim 1, wherein the HCDR1, the HCDR2 and the HCDR3 comprise amino acid sequences of SEQ ID NOs:19, 20 and 21, respectively, and the LCDR1, the LCDR2 and the LCDR3 comprise amino acid sequences of SEQ ID NOs: 22, 23 and 24, respectively.

7. The isolated antibody of claim 6, wherein the antibody is humanized.

8. A pharmaceutical composition comprising the antibody of 6 and a pharmaceutically acceptable carrier.

9. A vector comprising a polynucleotide encoding an antibody of claim 6.

10. A host cell comprising the vector of claim 9.

11. The isolated antibody of claim 1, wherein the HCDR1, the HCDR2 and the HCDR3 comprise amino acid sequences of SEQ ID NOs:7, 8 and 9, respectively, and the LCDR1, the LCDR2 and the LCDR3 comprise amino acid sequences of SEQ ID NOs: 10, 11 and 12, respectively.

12. The isolated antibody of claim 11, wherein the antibody is humanized.

13. A pharmaceutical composition comprising the antibody of 11 and a pharmaceutically acceptable carrier.

14. A vector comprising a polynucleotide encoding an antibody of claim 11.

15. A host cell comprising the vector of claim 14.

16. An isolated polynucleotide encoding an antibody heavy chain comprising a VH of the antibody of claim 11.

17. An isolated polynucleotide encoding an antibody light chain comprising a VL of the antibody of claim 11.

18. A host cell comprising the isolated polynucleotide of claim 16 or 17.

* * * * *